US007960133B2

(12) United States Patent
Al Hendy

(10) Patent No.: US 7,960,133 B2
(45) Date of Patent: Jun. 14, 2011

(54) METHODS OF DIAGNOSING LEIOMYOMA BY MEASURING CATECHOL-O-METHYLTRANSFERASE

(75) Inventor: Ayman Al Hendy, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/185,667

(22) Filed: Aug. 4, 2008

(65) Prior Publication Data

US 2009/0053207 A1 Feb. 26, 2009

Related U.S. Application Data

(62) Division of application No. 10/570,094, filed as application No. PCT/US2004/028989 on Sep. 7, 2004, now abandoned.

(60) Provisional application No. 60/500,078, filed on Sep. 4, 2003.

(51) Int. Cl.
    *C12Q 1/48* (2006.01)
(52) U.S. Cl. .......................................... 435/15; 435/7.1
(58) Field of Classification Search .................... 435/15, 435/7.1
    See application file for complete search history.

(56) References Cited

U.S. PATENT DOCUMENTS

| 5,633,371 | A * | 5/1997 | Bernauer et al. .............. 544/105 |
| 6,258,827 | B1 | 7/2001 | Chenard et al. ............... 514/327 |
| 2002/0006653 | A1 | 1/2002 | Meyers et al. ................. 435/193 |
| 2003/0100476 | A1 | 5/2003 | Weinberger et al. .............. 514/1 |
| 2003/0190381 | A1 * | 10/2003 | Bland et al. .................... 424/757 |
| 2003/0199472 | A1 | 10/2003 | Al-Hendy et al. ............... 514/44 |

OTHER PUBLICATIONS

Huber A., et al. Ten Estrogen Related Polymorphisms and Endometriosis. Obstetrics & Gynecology 106(5 Pt. 1)1025-1031, Nov. 2005.*
Lu, H. et al. Enzymology of Methylation of Tea Catechins and Inhibition of COMT . . . Drug Metabolism and Metabolism 31(5)572-579, 2005.*
Garner E. et al. Polymorphisms of the Estrogen Metabolizing Genes CYP17 and Catechol-O-Methyltransferase and Risk of Epithelial Ovarian Cancer. Cancer Research 3058-3062, Jun. 1, 2002.*
Vangala V. et al. Synthesis of Catechol Estrogens by Human Uterus and Leiomyoma. Steroids 37(2)195-203, Feb. 1981.*
Al-Hendy and Luxon et al., "Differential RNA Microarray Analysis of Normal Human Myometrium, Smal and Large Leiomyoma," *J. Soc. Gynecol. Investig.*, 9(1):307, 2002 (Abstract No. 744).
Al-Hendy and Salama, "Catechol-O-methyltransferase polymorphism is associated with increased uterine leiomyoma risk in different ethnic groups," *J. Soc. Gynecol. Investig.*, 13:136-144, 2006.

Al-Hendy and Salama, "Ethnic distribution of estrogen receptor-alpha polymorphism is associated with a higher prevalence of uterine leiomyomas in black Americans," *Fertil. Steril.*, 86:686-693, 2006.
Al-Hendy and Salama, "Gene therapy and uterine leiomyoma: a review," *Human Reproduction Update*, 12:385-400, 2006.
Andersen et al., "Leiomyoma Primary Cultures Have Elevated Transcriptional Response to Estrogen Compared with Autologous Myomtrial Cultures," *J. Soc. Gynecol. Investig.*, 2:542-551, 1995.
Balloch, "The relative frequency of fibroid processes in the dark-skinned races," *Medical News*, LXIV:29-35, 1894.
Barchiesi et al., "2-Methoxyestradiol inhibits human aortic smooth muscle cell growth via double blockade of cell-cycle and modulation of cell-cycle regulators," *Hypertension*, 42:415, 2003 (P57, abstract).
Barchiesi et al., "Methoxyestradiols Mediate Estradiol-Induced Antimitogenesis in Human Aoritc SMCs," *Hypertension*, 39:874-879, 2002.
Bertelli et al., "Antiplatelet Activity of CIS-Resveratrol," *Drugs Explt. Clin. Res.*, XXII:61-63, 1996.
Bonifacio et al., "Catechol-O-methyltransferase and its inhibitors in Parkinson's disease," *CNS Drug Reviews*, 13:352-379, 2007.
Brandon et al., "Estrogen Receptor Gene Expression in Human Uterine Leiomyomata," *J. Clin. Endocrinol. Metab.*, 80:1876-1881, 1995.
Chappell et al., "Effect of antioxidants on the occurrence of pre-eclampsia in women at increased risk: a randomised trial," *LANCET*, 354:810-816, 1999.
Chegini et al., "Gene Expression Profile of Leiomyoma and Myometrium and the Effect of Gonadotropin Releasing Hormone Analogue Therapy,"*J. Soc. Gynecol. Investig.*, 10:161-171, 2003.
Cramer and Patel, "The frequency of uterine leiomyomas," *Am. J. Clin. Pathol.*, 94(4):435-8, 1990.
Dawood et al., "Cortical and trabecular bone mineral content in women with endometriosis: effect of gonadotropin-releasing hormone agonist and danazol," *Fertil. Steril.*, 52:21-26, 1989.
Deligdish and Loewenthal, "Endometrial changes associated with myomata of the uterus," *J. Clin. Pathol.*, 23:676-680, 1970.
Dubey et al., "Clinically Used Estrogens Differentially Inhibit Human Aortic Smooth Muscle Cell Growth and Mitogen-Activated Protein Kinase Activity," *Arterioscler. Thromb. Vasc. Biol.*, 20:964-972, 2000.
Frisch et al., "Association of anorexia nervosa with the high activity allele of the COMT gene: a family-based study in Israeli patients," *Mol. Psychiatry*, 6:243-245, 2001.
Fuchs-Young et al., "Inhibition of estrogen-stimulated growth of uterine leiomyomas by selective estrogen receptor modulators,"*Mol. Carcinog.*, 17:151-159, 1996.
Goodman et al., "Case-Control Study of Ovarian Cancer and Polymorphisms in Genes Inolved in Catecholestrogen Formation and Metabolism," *Cancer Epidemiology Biomarkers & Prevention*, 10:209-216, 2001.

(Continued)

*Primary Examiner* — Ralph Gitomer
(74) *Attorney, Agent, or Firm* — Fulbright & Jaworski L.L.P.

(57) ABSTRACT

The present invention relates to an association between specific polymorphisms of the COMT polypeptide and the development, or risk of developing, preterm labor and uterine diseases and conditions. Disclosed are therapeutic, preventative and diagnostic methods and compositions relating to pre-term labor, uterine diseases and conditions, and ovarian conditions and diseases. In certain embodiments, such methods and compositions involve a COMT inhibitor.

18 Claims, 13 Drawing Sheets

OTHER PUBLICATIONS

Goodman et al., "COMT genotype, micronutrients in the folate metabolic pathway and breast cancer risk," *Carcinogenesis*, 22:1661-1665, 2001.

Gordon et al., "Amenorrhea and bone health in adolescents and young women," *Curr. Opin. Obstet. Gynecol.*, 15(5):377-384, 2003.

Gutpa et al., "Estrogenic and antiestrogenic activities of 16alpha- and 2-hydroxy metabolites of 17beta-estradiol in MCF-7 and T47D human breast cancer cells," *J. Steroid Biochem. Mol. Biol.*, 67(5-6):413-419, 1998.

Haram et al., "Preterm delivery: an overview," *Acta. Obstet. Gynecol. Scand.*, 82:687-704, 2003.

Howe et al., "Rodent model of reproductive tract leiomyomata. Establishment and characterization of tumor-derived cell lines," *Am. J. Pathol.*, 146:1568-1579, 1995.

Hsieh et al., "Estrogen receptor thymine-adenine dinucleotide repeat polymorphism is associated with susceptibility to leiomyoma," *Fertil. Steril.*, 79:96-99, 2003.

Huang et al., "Breast cancer risk associated with genotype polymorphism of the estrogen-metabolizing genes CYP17, CYP1A1, and COMT: a multigenic study on cancer susceptibility," *Cancer Res.*, 59:4870-4875, 1999.

Kitawaki et al., "Oestrogen receptor-alpha gene polymorphism is associated with endometriosis, adenomyosis and leiomyomata," *Hum. Reprod.*, 16:51-55, 2001.

Kjerulff et al., "Hysterectomy and race," *Obstet. Gynecol.*, 82:757-764, 1993.

Kola et al., "Co-administration of ascorbic acid with cyclophosphamide (CPA) to pregnant mice inhibits the clastogenic activity of CPA in preimplantation murine blastocysts," *Mutagenesis*, 4:297-301, 1989.

Lachman et al., "Human catechol-O-methyltransferase pharmacogenetics: description of a functional polymorphism and its potential application to neuropsychiatric disorders," *Pharmacogenetics*, 6:243-250, 1996.

Lal et al., Combined Antioxidant and COMT inhibitor treatment reverses renal abnormalities in diabetic rats, *Diabetes*, 49:1381-1389, 2000.

Lavigne et al., "An association between the allele coding for a low activity variant of catechol-O-methyltransferase and the risk for breast cancer," *Cancer Research*, 57:5493-5497, 1997.

Lethaby et al., "Pre-operative GnRH analogue therapy before hysterectomy or myomectomy for uterine fibroids (Cochrane Review)," *The Cochrane Library*, Oxford: Update Software Ltd., Issue 1, 2003 (Abstract).

Linde, In: *Operative Gynecology*, Rock and Thompson (Eds.), Philadelphia: Lippincott-Raven; 732-770, 1997.

Marshall et al., "Variation in the incidence of uterine leiomyoma among premenopausal women by age and race," *Obstet. Gynecol.*, 90:967-973, 1997.

Massart et al., "Genotype distribution of estrogen receptor-alpha gene polymorphisms in Italian women with surgical uterine leiomyomas," *Fertil. Steril.*, 75:567-570, 2001.

Matsuo et al., "Increased expression of Bcl-2 protein in human uterine leiomyoma and its up-regulation by progesterone," *J Clin Endocrinol Metab.*, 82:293-299, 1997.

McLeod et al., "Ethnic differences in erythrocyte catechol-O-methyltransferase activity in black and white Americans," *J. Pharmacol. Exp. Ther.*, 270:26-29, 1994.

Mitrunen et al., "Polymorphic catechol-O-methyltransferase gene and breast cancer risk," *Cancer Epidemiol. Biomarkers Prev.*, 10:635-640, 2001.

Nowak, "Identification of New Therapies for Leiomyomas: What In Vitro Studies Can Tell Us," *Clin. Obstet. Gynecol.*, 44(2):327-334, 2001.

Office Communication, dated Oct. 14, 2008.

Patrikis et al., "Mutation analysis of CDP, TP53, and KRAS in uterine leiomyomas," *Mol. Carcinog.*, 37:61-64, 2003.

Pollow et al., "In Vitro Conversion of Estradiol-17beta into Estrone in Normal Human Myoetrium und Leiomyoma," *J. Cline. Chem. Clin. Biochem.*, 16:493-502, 1978.

Ramakrishnan et al., "Micronutrients and pregnancy outcome: a review of the literature," *Nutrition Research*, 19:103-159, 1999.

Reddy et al., "Synthesis of catechol estrogens by human uterus and leiomyoma," *Steroids*, 37:195-203, 1981.

Reenila, "Catechol-O-Methyltransferase Activity: Assay, Distribution and Pharmacological Modification," Doctoral Dissertation presented to the Medical Faculty of the University of Helsinki, 1999.

Rich, "Cancer of the Uterus," www.gyncancer.com/uterus.html, Aug. 8, 2003.

Salama et al., "Estrogen metabolite 2-methoxyestradiol induces apoptosis and inhibits cell proliferation and collagen production in rat and human leiomyoma cells: a potential medicinal treatment for uterine fibroids," *J. Soc. Gynecol. Investig.*, 13:542-550, 2006.

Salama et al., "Hormonal regulation of catechol-O-methyl transferase activity in women with uterine leiomyomas," *Fertil. Steril.*, 86:259-262, 2006.

Schimmel, "National Foudnation for Cancer Research: Page Server Uterine cancer information," www.nfcr.org/site/PageServer?pagename=cancers_uterine&printer_friendly=1, 2 pages, Aug. 8, 2003.

Schutze et al., "Catecholestrogens are MCF-7 cell estrogen receptor agonists," *J. Steroid Biochem. Mol. Biol.*, 46(6):781-789, 1993.

Siega-Rit et al., "Vitamin C intake and the risk of preterm delivery," *Am. J. Obstet. Gynecol.*, 189:519-525, 2003.

Thompson et al., "Genetic polymorphisms in catechol-O-methyltransferase, menopausal status, and breast cancer risk," *Cancer Res.*, 58:2107-2110, 1998.

Torpin et al., "The Etiologic and Pathologic Factors in a Seires of 1,741 Fibromyomas of the Uterus," *Am. J. Obstet. Gynecol.*, 44:569-574, 1942.

Tsibris et al., "Insights from gene arrays on the development and growth regulation of uterine leiomyomata," *Fertil. Steril.*, 78:114-121, 2002.

Weismiller, "Preterm Labor," *AAFP*, 59(3):593-602, 1999.

Wentz et al., "Regulation of Catechol-O-Methyltransferase Expression in Human Myometrial Cells," *Obstetrics & Gynecology*, 108:1439-1447, 2006.

Wilcox et al., "Serotonin regulation of interleukin-1 messenger RNA in rat uterine smooth muscle cells. Relationship to the production of interstitial collagenase," *J. Biol. Chem.*, 269:29658-29664, 1994.

Wilson, "Pathogenesis of polycystic kidney disease: altered cellular function," In : *Polysystic Kidney Disease*, Watson and Torres (Eds.), Oxford Medical Publications, 125-163, 1996.

Witherspoon and Butler, "The Etiology of Uterine Fibroids," *Surg. Gynecol. Obstet.*, 58:57-61, 1934.

Xie et al., "Characterization and implications of estrogenic down-regulation of human catechol-O-methyltransferase gene transcription," *Mol. Pharmacol.*, 56:31-38, 1999.

Xie, et al, "Genetic polymorphisms of catechol-O-methyltransferase and the risk of breast cancer: The Shanghai Breast Cancer Study," *Proc. Am. Assoc. Cancer Res.*, 40:567, Abstract No.: 3744, 1999.

Yim et al., "Relationship between the Val158Met polymorphism of catechol o-methyl transferase and breast cancer," *Pharmacogenetics*, 11:279-286, 2001.

Zacharia et al., "Methoxyestradiols Mediate the Antimitogenic Effects of 17beta-Estradiol: Direct Evidence From Catechol-O-Methyltransferase-Knockout Mice," *Circulation*, 108(24):2974-2978, 2003.

Zaloudek and Hendrickson, "Mesenchymal Tumors of the Uterus," In: *Blaustetin's Pathology of the Female Fenital Tract*, Springer-Verlag (Ed.), 5th Ed., NY 561-615, 2002.

Zhu and Conney, "Functional role of estrogen metabolism in target cells: review and perspectives," *Carcinogenesis*, 19:1-27, 1998.

Zhu and Liehr, "Inhibition of Catechol O-Methyltransferase-catalyzed O-Methylation of 2- and 4-Hydroxyestradiol by Quercetin," *J. Biol. Chem.*, 271:1357-1363, 1996.

Zhu, "Catechol-O-Methyltransferase (COMT)-mediated methylation metabolism of endogenous bioactive catechols and modulation by endobiotics and xenobiotics: importance in pathophysiology and pathogenesis," *Curr Drug Metab.*, 3(3):321-349, 2002.

* cited by examiner

SEQUENCE LISTING

<160> NUMBER OF SEQ ID NOS: 4

<210> SEQ ID NO 1
<211> LENGTH: 1217
<212> TYPE: DNA
<213> ORGANISM: Homo sapiens
<220> FEATURE:
<221> NAME/KEY: CDS
<222> LOCATION: (445)..(993)

<400> SEQUENCE: 1

```
ggcttctggg gcagctaggg ctgcccgccg cgctgcctgc gccggaccgg ggcgggtcca      60
gtcccgggcg ggccgtcgcg ggagagaaat aacatctgct ttgctgccga gctcagagga     120
gaccccagac ccctcccgca gccagagggc tggagcctgc tcagaggtgc tttgaagatg     180
ccggaggccc cgcctctgct gttggcagct gtgttgctgg gcctggtgct gctggtggtg     240
ctgctgctgc ttctgaggca ctggggctgg ggcctgtgcc ttatcggctg gaacgagttc     300
atcctgcagc ccatccacaa cctgctcatg ggtgacacca aggagcagcg catcctgaac     360
catgtgctgc agcatgcgga gcccgggaac gcacagagcg tgctggaggc cattgacacc     420
tactgcgagt agaaggagtg ggcc atg aac gtg ggc gac aag aaa ggc aag       471
                            Met Asn Val Gly Asp Lys Lys Gly Lys
                              1               5 atc gtg gac gcc gtg att cag gag cac cag ccc tcc gtg ctg ctg gag      519
Ile Val Asp Ala Val Ile Gln Glu His Gln Pro Ser Val Leu Leu Glu
```

```
                    10                  15                  20                  25
ctg ggg gcc tac tgt ggc tac tca gct gtg cgc atg gcc cgc ctg ctg         567
Leu Gly Ala Tyr Cys Gly Tyr Ser Ala Val Arg Met Ala Arg Leu Leu
                30                  35                  40 tca cca ggg gcg agg ctc atc acc atc gag atc aac ccc gac tgt gcc         615
Ser Pro Gly Ala Arg Leu Ile Thr Ile Glu Ile Asn Pro Asp Cys Ala
            45                  50                  55 gcc atc acc cag cgg atg gtg gat ttc gct ggc atg aag gac aag gtc         663
Ala Ile Thr Gln Arg Met Val Asp Phe Ala Gly Met Lys Asp Lys Val
                60                  65                  70 acc ctt gtg gtt gga gcg tcc cag gac atc atc ccc cag ctg aag aag         711
Thr Leu Val Val Gly Ala Ser Gln Asp Ile Ile Pro Gln Leu Lys Lys
        75                  80                  85 aag tat gat gtg gac aca ctg gac atg gtc ttc ctc gac cac tgg aag         759
Lys Tyr Asp Val Asp Thr Leu Asp Met Val Phe Leu Asp His Trp Lys
90                  95                  100                 105 gac cgg tac ctg ccg gac acg ctt ctc ttg gag gaa tgt ggc ctg ctg         807
Asp Arg Tyr Leu Pro Asp Thr Leu Leu Leu Glu Glu Cys Gly Leu Leu
                110                 115                 120 cgg aag ggg aca gtg cta ctg gct gac aac gtg atc tgc cca ggt gcg         855
Arg Lys Gly Thr Val Leu Leu Ala Asp Asn Val Ile Cys Pro Gly Ala
            125                 130                 135 cca gac ttc cta gca cac gtg cgc ggg agc agc tgc ttt gag tgc aca         903
Pro Asp Phe Leu Ala His Val Arg Gly Ser Ser Cys Phe Glu Cys Thr
                140                 145                 150 cac tac caa tcg ttc ctg gaa tac agg gag gtg gtg gac ggc ctg gag         951
His Tyr Gln Ser Phe Leu Glu Tyr Arg Glu Val Val Asp Gly Leu Glu
            155                 160                 165 aag gcc atc tac aag ggc cca ggc agc gaa gca ggg ccc tga               993
Lys Ala Ile Tyr Lys Gly Pro Gly Ser Glu Ala Gly Pro
170                 175                 180 ctgccccccc cggcccccct ctcgggctct ctcacccagc ctggtactga aggtgccaga      1053
cgtgctcctg ctgaccttct gcggctccgg gctgtgtcct aaatgcaaag cacacctcgg      1113
ccgaggcctg cgccctgaca tgctaacctc tctgaactgc aacactggat tgttcttttt      1173
taagactcaa tcatgacttc tttactaaaa aaaaaaaaaa aaaa                      1217

<210> SEQ ID NO 2
<211> LENGTH: 182
<212> TYPE: PRT
<213> ORGANISM: Homo sapiens

<400> SEQUENCE: 2

Met Asn Val Gly Asp Lys Lys Gly Lys Ile Val Asp Ala Val Ile Gln
1               5                   10                  15

Glu His Gln Pro Ser Val Leu Leu Glu Leu Gly Ala Tyr Cys Gly Tyr
                20                  25                  30

Ser Ala Val Arg Met Ala Arg Leu Leu Ser Pro Gly Ala Arg Leu Ile
            35                  40                  45

Thr Ile Glu Ile Asn Pro Asp Cys Ala Ala Ile Thr Gln Arg Met Val
        50                  55                  60

Asp Phe Ala Gly Met Lys Asp Lys Val Thr Leu Val Val Gly Ala Ser
65                  70                  75                  80

Gln Asp Ile Ile Pro Gln Leu Lys Lys Lys Tyr Asp Val Asp Thr Leu
                85                  90                  95

Asp Met Val Phe Leu Asp His Trp Lys Asp Arg Tyr Leu Pro Asp Thr
                100                 105                 110

Leu Leu Leu Glu Glu Cys Gly Leu Leu Arg Lys Gly Thr Val Leu Leu
```

```
                        115                 120                 125
Ala Asp Asn Val Ile Cys Pro Gly Ala Pro Asp Phe Leu Ala His Val
    130                 135                 140

Arg Gly Ser Ser Cys Phe Glu Cys Thr His Tyr Gln Ser Phe Leu Glu
145                 150                 155                 160

Tyr Arg Glu Val Val Asp Gly Leu Glu Lys Ala Ile Tyr Lys Gly Pro
                165                 170                 175

Gly Ser Glu Ala Gly Pro
            180

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
ctcatcacca tcgagatcaa                                                     20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
ccaggtctga caacgggtca                                                     20
```

METHODS OF DIAGNOSING LEIOMYOMA BY MEASURING CATECHOL-O-METHYLTRANSFERASE

The present application is a divisional application of and claims priority to U.S. patent application Ser. No. 10/570,094 filed on 30 Nov. 2006 now abandoned, which is a national phase application under 35 U.S.C. §371 of International Application No. PCT/US2004/028989 filed 7 Sep. 2004, which claims priority to U.S. Provisional Application No. 60/500,078 filed 4 Sep. 2003 all of which are incorporated herein by reference in their entirety.

BACKGROUND OF THE INVENTION

A. Field of the Invention

The present invention relates generally to the fields of oncology, obstetrics, and gynecology. More particularly, it concerns diagnosing people at risk for developing uterine diseases, uterine conditions or pre-term labor. This invention further concerns methods of treating and preventing uterine diseases or conditions, ovarian diseases or conditions, and pre-term labor.

B. Description of Related Art

Preterm labor and uterine diseases and conditions pose serious health concerns in today's society. A number of women are subject to preterm labor that results in pregnancy complications affecting an estimated 8 to 10 percent of births in the United States each year (Weismiller, 1999). Moreover, it is estimated that 25-50% of all women are diagnosed with a uterine disease or condition in their lifetime.

1. Preterm Labor

Preterm labor refers to true labor occurring before the end of the 36th week of pregnancy and it is characterized by cervical effacement, dilatation and increased uterine irritability (Weismiller, 1999). Studies have shown that women with a history of previous preterm delivery are at a greater risk of recurrence (Weismiller, 1999).

Strategies to prevent preterm labor have focused on early diagnosis and on clinical markers (Weismiller, 1999). An example of some of the clinical markers have included monitoring cervical change, uterine contractions, bleeding and changes in fetal behavioral states (Weismiller, 1999). Despite evaluation of such markers, women continue to undergo pre-term labor with and without symptoms. The underlying mechanisms underlying preterm labor have yet to be elucidated and understood.

In fact, to date there has been no genetic information regarding women at risk for preterm labor, nor has there been any data involving specific polymorphisms that can arise in the COMT polypeptide and the likelihood of a woman developing preterm labor. Therefore, there is a need for better prognostic and diagnostic tests for women at risk for preterm labor, particularly a genetic-based test. Such a test can then be used to identify women at risk for preterm labor and increase the likelihood of successful treatment.

Current treatments for the prevention and treatment of preterm labor include the administration of an antibiotic, a tocolytic drug, a non-estradiol anti-inflammatory drug or a calcium channel blocker. Nonetheless, many women undergo preterm labor even if such treatments are administered. Consequently, there continues to be a need for improved therapeutic options for the treatment of preterm labor.

2. Uterine Diseases and Conditions

A uterine disease or condition can be characterized by a number of disorders ranging from adenomyosis, endometriosis, endometrial hyperplasia, leiomyosarcoma, benign tumor, malignant tumor, dysfunctional uterine bleeding, endometrial cancer, premenstrual syndrome or abnormal uterine bleeding. Known risk factors for developing a uterine disease such as uterine cancer, for example, include prolonged estrogen exposure, early menarche, late menopause, no children, failure to ovulate and obesity. Suggested prevention measures for people determined to be at risk for developing a uterine cancer have been identified as including maintaining an ideal weight, annual pelvic exams and endometrial biopsy at menopause.

Leiomyomas (fibroids) are benign smooth-muscle cell (SMC) tumors of the uterus and are the most common pelvic tumors in women. These tumors occur primarily during the reproductive years and are the most common indication for hysterectomy in women. Unfortunately, alternative therapies are few and hysterectomy or myomectomy being the treatment of choice in most cases (Martel et al., 2004). The discovery and development of medicinal therapies for uterine leiomyoma have been hampered by a lack of understanding regarding the etiology and molecular mechanisms underlying the development of these lesions. Although the precise pathophysiology of fibroids is unknown, several endogenous or environmental factors that modulate risk for developing uterine leiomyoma affirm the hormone responsive nature of this disease. Early Menarche, African-American ethnicity, nulliparity, and obesity are among the common risk factors for Leiomyomas. The impact of many of these factors has often been attributed to their effects upon estrogen and progesterone levels or metabolism that may in part reflect aspects of a woman's hormonal milieu (Gordon et al., 2003). Furthermore, another potential mechanism for development of leiomyomas is a decrease in apoptosis. Matsuo et al. (1997) found that Bcl-2 protein, an apoptosis-inhibiting gene product, was abundantly expressed in leiomyomata relative to that in normal myometrium.

In some studies, it was suggested that a specific COMT polymorphism at position 108 of the COMT polypeptide (Val108→Met108) appears to be associated with an increased risk of breast cancer and Parkinson's disease in humans. (Zhu, 2002; Lavigne et al., 1997; Thompson et al., 1998; Huang et al., 1999; Yim et al.; 2001; Xie et al.; 1999; Mitrunen et al.; 2001 and Goodman et al, 2001). Another study examined the relationship between the COMT polymorphism (Val158→Met158) and the development of anorexia nervosa in patients. (Frisch et al., 2001; Zhu 2002). However, no such information has been suggested with respect to uterine diseases or conditions.

One study that used enzyme activity to predict subject phenotype (McLeod et al., 1994) observed no gender difference in COMT enzymatic activity. Due to high prevalence of uterine leiomyomas (77% in autopsy studies) (Cramer and Patel, 1990), and relatively young age of women in McLeod et al. (1994) (34-36 years), it was apparent that several of the volunteer subjects were harboring either non-symptomatic or pre-symptomatic uterine leiomyomas.

Developments of therapeutic agents which are capable of reversing the tumor growth in Leiomyomas without the unwanted side effects are urgently needed for the conservative treatment of Leiomyomas. Pharmacological agents that modulate the hormonal milieu and target the growth factors and apoptotic/antiapoptotic could be a useful treatment for Leiomyomas. It has been suggested that there is a similarities between the biology of leiomyomas and other SMCs disease such as atherosclerosis (Nowak, 2001).

2-Methoxyestradiol (2-MeO-$E_2$) is a nonpolar endogenous $E_2$ metabolite formed by the COMT-mediated O-methylation of 2-hydroxyestradiol, a major catechol $E_2$ metabolite formed in humans (Zhu and Conney 1998a,b). Recent study suggested that 2-Methoxyestradiol inhibited DNA synthesis, cell numbers, and collagen synthesis in SMCs (Zacharia et al., 2003). 2-Methoxyestradiol binds at the colchicine-binding site of tubulin and disrupts tubulin polymerization, a process essential for cell division. Also, 2-methoxyestradiol blocks SMC growth in both $G_0/G_1$ and $G_2/M$ phases of the cell cycle, by inhibiting cyclin-$D_1$ and cyclin-$B_1$ expression (Barchiesi et al., 2003). Moreover, 2-methoxyestradiol inhibits phosphorylation of retinoblastoma protein, ERK1/2 (MAPK) (Dubey et al., 2000) and upregulates Cdk inhibitor p27 (Barchiesi et al., 2003). Because 2-methoxyestradiol has a low systematic toxicity, considerable research efforts have been initiated lately to explore the usefulness of 2-MeO-$E_2$ as a low-toxicity chemotherapeutic agent for human breast cancer as well as for other cancers. Currently, larger-scale clinical trials are underway to evaluate the effectiveness of 2-MeO-$E_2$ as an antitumor agent in prostate and breast cancer.

However, to date, there has been evidence that such treatments can be used for genitourinary conditions or diseases. Nor have there been any studies suggesting a correlation between specific polymorphisms that can arise in the COMT polypeptide and the likelihood of developing a genitourinary disease or condition, such as a uterine cancer. Furthermore, while some treatment for genitourinary conditions—such as uterine diseases and conditions—exist, women continue to suffer from these diseases and conditions. Thus, diagnostic tests are needed to identify women at risk for developing a genitourinary condition or disease, and improved treatment options are similarly desirable.

SUMMARY OF THE INVENTION

The inventors discovered an association between specific polymorphisms of the COMT polypeptide and the development, or risk of developing, preterm labor and uterine diseases and conditions. Accordingly, the present invention concerns therapeutic, preventative and diagnostic methods and compositions relating to genitourinary disorders, including pre-term labor, ovarian diseases and conditions, and uterine diseases and conditions. Other conditions such as osteoporosis, pelvic organ prolapse, breast cancer, liver cancer, intrauterine growth restriction and pre-eclampsia can also be treated, prevented and/or diagnosed in a patient according to the present invention. Further, the present invention can be used to prevent or induce cervical ripping in a patient. Also disclosed are methods of screening for modulators of the COMT polypeptide. The term "COMT" as that term is used in the specification and claims encompasses all forms of COMT, including membrane bound COMT (MB-COMT) and soluble COMT (S-COMT).

The term "genitourinary disorder" refers to a disturbance of a genitourinary bodily function and includes ailments, conditions, and diseases. These disorders affect the organs, tissues, and cells in a woman's abdominal and pelvic areas, and it includes the vulva, vagina, uterus, ovaries, cervix, fallopian tubes, bladder, rectum and lower intestines. It is contemplated that such disorders can include those that afflict a woman who is having difficulty getting pregnant (female infertility), is pregnant or who has given birth. Thus, such disorders include pregnancy and post-partum conditions, ailments and diseases.

The present invention includes methods of preventing or treating one or more genitourinary disorders, which includes pre-term labor, intrauterine growth restriction, osteoporosis, pelvic organ prolapse, breast cancer, liver cancer, pre-eclampsia, ovarian diseases or conditions, and/or uterine diseases or conditions in a patient. Such methods can also be applied to female infertility problems, including unexplained infertility. Such methods can include administering an effective amount of a COMT inhibitor to the patient in need of the inhibitor. It is contemplated that the present invention can also be used to prevent cervical ripping in a patient. The term "uterine disease or condition" as used in the specification and the claims includes such conditions and diseases as adenomyosis, endometriosis, endometrial hyperplasia, leiomyosarcoma, benign tumor, malignant tumor, dysfunctional uterine bleeding, endometrial cancer, premenstrual syndrome or abnormal uterine bleeding. The term "ovarian disease or condition" as used in the specification and the claims includes such diseases and conditions as polycystic ovary syndrome, anovulation, premature ovarian failure, ovarian causes of infertility, and irregular ovulation.

The term "COMT inhibitor" refers to a substance that directly or indirectly inhibits the activity of COMT in an organism. Consequently, the substance may inhibit, prevent, preclude, and/or reduce binding activity, specificity, catalytic activity, translocation, transcription, translation, post-translational modification, transport, and/or transcript or protein stability of COMT. The inhibitors may be nucleic acids, proteins (peptides or polypeptides), analogs thereof, small molecules, or any other agent or chemical that modifies the COMT-encoding nucleic acid, COMT protein, or its activity. Examples of COMT inhibitors are well known and they include, but are not limited to, those disclosed herein. The inhibitor may also be a prodrug, meaning it is converted to an COMT inhibitor by metabolic processes.

Methods of the invention can be diagnostic, preventative, and/or therapeutic. In some embodiments, the methods are diagnostic only, meaning the method is used to identify a patient at risk of the condition or disease or having the condition or disease. In other embodiments, the methods are preventative, meaning the method is used to prevent the patient from developing a particular disease or condition. Moreover, in other embodiments, the invention is therapeutic, meaning the method is used to treat a condition or disease in the patient. It is specifically contemplated that any or all of these methods may be combined with one another. For example, a diagnostic method of the invention can be combined with a therapeutic method of the invention, though it is specifically contemplated that each method may be implemented on its own.

In particular aspects, the methods also include determining whether a patient is in need of the prevention or treatment. This can include determining whether a patient is at risk for developing a genitourinary disorder or has symptoms of a genitourinary disorder. In certain embodiments, methods are directed to evaluating the risk of pre-term labor, intrauterine growth restriction, pre-eclampsia and/or a uterine disease or condition. Determining whether a patient is at risk for developing such conditions or has the condition can include taking a family history or a patient history. In other embodiments, diagnostic methods of the invention discussed below are used to determine whether the patient is at risk for developing a genitourinary disorder, such as a uterine condition or disease or at risk for undergoing preterm labor.

In particular aspects of this invention, the patient was previously diagnosed as being at risk for preterm labor or a uterine condition or disease or the patient is exhibiting symptoms of pre-term labor, intrauterine growth restriction, pre-eclampsia, polycystic ovary syndrome (PCOS), female infertility secondary to anovulation, and/or a uterine disease or condition or was previously treated and/or diagnosed for such conditions. With respect to the treatment or prevention of pre-term labor, intrauterine growth restriction or pre-eclampsia, the patient can be pregnant and exhibiting symptoms of pre-term labor, intrauterine growth restriction and/or pre-eclampsia. Alternatively, the patient may be exhibiting or have signs of polycystic ovary syndrome or female infertility secondary to anovulation. These symptoms include absent menstruation or irregular menstruation, and infertility. Ultrasound can confirm the existence of PCOS.

In particular embodiments, the uterine disease or condition is a uterine tumor. The uterine tumor can be a leiomyoma that is submucous, intramural or subserous fibroid.

The patient in need of the prevention or treatment can have a first allele encoding a valine at position 158 and a second allele encoding a valine at position 158 of a COMT polypeptide. In other embodiments, the patient in need of the prevention or treatment has a first allele encoding a valine at position 158 and a second allele encoding a methionine at position 158 of a COMT polypeptide.

The COMT inhibitor(s) used to prevent or treat a patient according to the present invention can be a polypeptide, a nucleic acid or a small molecule. The COMT inhibitor(s) can directly or indirectly decrease the amount or activity of a COMT polypeptide. In certain embodiments, the COMT inhibitor inhibits the transcription, translation and/or the expression of COMT. In other aspects, the COMT inhibitor can be an antagonist of COMT. The antagonist can be an antibody composition comprising an antibody that recognizes a COMT polypeptide. The antibody can be a polyclonal antibody, monoclonal antibody, humanized antibody, single chain antibody, antibody fragment such as a Fab, or a bi-specific antibody. Molecules containing a 5-nitrocatechol moiety such as entacapone, nitecapone, tocapone and Ro 41-0960 are contemplated as COMT inhibitors that can be used with the invention. In more particular embodiments of this invention, the COMT inhibitor(s) is Tasmar or Comtan.

In further aspects of this invention, the methods also include administering a second therapy used to treat or prevent pre-term labor, intrauterine growth restriction and/or pre-eclampsia. Second therapies that can be used to treat or prevent pre-term labor, intrauterine growth restriction and/or pre-eclampsia include bed rest or a composition comprising an antibiotic, a tocolytic drug, a non-estradiol anti-inflammatory drug or a calcium channel blocker. The tocolytic drug can be ritodrine, terbutaline or magnesium sulfate. The non-estradiol anti-inflammatory drug can be indomethacine. The calcium channel blocker can be nifedipine. Non-limiting examples of the antibiotics that can be used with this invention include penicillin, erythromycin, ampicillin or clindamycin. Additional antibiotics that are known in the art can also be used with this invention.

Second therapies that can be used to treat or prevent a uterine disease or condition include radiation therapy, chemotherapy, hormonal therapy, immunotherapy, surgery, gene therapy and/or hyperthermia. In particular embodiments, the second therapy is hormonal therapy. The hormonal therapy comprises administering a COMT inhibitor to the patient in some embodiments of the invention. Moreover, in other embodiments the COMT inhibitor is administered in conjunction (before, after, or at the same time) with a therapy involving 2-methoxyestradiol.

In further aspects of this invention, the methods also include administering a second therapy used to treat ovarian conditions or diseases. Second therapies that can be used to treat these conditions or diseases include ovulation medications (clomiphene, follistim, Gonal-F), ovarian drilling surgery, and IVF. Symptoms have been managed by anti-androgen medication (birth control pills, spironolactone, flutamide or finasteride), which can be administered as a second therapy in embodiments of the invention.

The second therapies can be administered to a patient before, after, or at the same time as COMT inhibitors of the invention.

Other aspects of the present invention include methods of determining whether a patient is at risk for developing pre-term labor, intrauterine growth restriction, pre-eclampsia and/or a uterine disease or condition comprising identifying the amino acid at position 158 of at least a first COMT polypeptide obtained from the patient, wherein identifying a valine indicates that the patient is at risk for developing a uterine tumor. Due to the fact that each patient will have two COMT alleles, it is contemplated that the sequence of one or both alleles may be determined in the patient by determining the amino acid sequence of one or both types of COMT polypeptides that are the result of each allele. It is further contemplated that the amino acid sequence at or at least at 1, 2, 3, 4, 5, 6, 7, 8, 9 10 or more residues within one or both types of COMT polypeptides may be determined. In specific embodiments, the amino acid sequence at position 158 is determined in the polypeptide of one allele, while in other embodiments, the amino acid sequence at position 158 is determined for polypeptides of both alleles.

The methods can further include obtaining a sample from the patient. Samples include, but are not limited to, blood, serum, pap smears, swabs, lavages, biopsies, or other biological materials obtained from the patient.

In particular aspects, the uterine disease or condition is a uterine tumor. The uterine tumor can be a leiomyoma that is submucous, intramural or subserous fibroid. These methods can also comprise identifying the amino acid at position 158 of a second COMT polypeptide obtained from the patient, wherein identifying a valine at position 158 of the second COMT polypeptide indicates that the patient is at an increased risk for developing a uterine disease or condition. The term increased, and any variations of that term, when used in the specification and claims means that a person having two alleles that encode a valine at position 158 of a COMT polypeptide has an increased risk of developing pre-term labor, intrauterine growth restriction, pre-eclampsia and/or a uterine disease or condition when compared to a patient that does not have two alleles encoding for a valine at position 158 of a COMT polypeptide. Alternatively, identifying the amino acid at position 158 of a second COMT polypeptide obtained from the patient, wherein identifying a methionine at position 158 of the second COMT polypeptide indicates that the patient is at risk for developing a uterine disease or condition.

In some embodiments, identifying the amino acid at position 158 of a COMT polypeptide comprises determining the nucleic acid sequence of a first COMT gene, wherein the sequencing encodes for the amino acid at position 158 of the COMT polypeptide. In other embodiments, determining the nucleic acid sequence comprises sequencing the nucleic acid sequence encoding the amino acid at position 158 of the COMT polypeptide. The nucleic acid being sequenced can be a genomic sequence or it can be a cDNA sequence. Identifying the amino acid at position 158 of the COMT polypeptide can also comprise determining the identity of a nucleic acid sequence in linkage disequilibium with the nucleic acid sequence encoding an amino acid at position 158 of the COMT polypeptide. The term "linkage disequilibrium" as used in the claims and the specification, refers to a phenomenon wherein alleles tend to remain together in linkage groups when segregating from parents to offspring, with a greater frequency than expected from their individual frequencies. Identifying the amino acid at position 158 of the COMT polypeptide can comprise differentiating a nucleic acid sequence encoding a valine from a nucleic acid sequence encoding a methionine at position 158 of the COMT polypeptide obtained from the patient.

In still other embodiments, determining whether a patient is at risk for developing pre-term labor, intrauterine growth restriction, pre-eclampsia and/or a uterine disease or condition further comprises taking a family history or a patient history. In particular embodiments, a patient is pregnant and exhibiting symptoms of pre-term labor, intrauterine growth restriction and/or pre-eclampsia.

Determining whether a patient is at risk for developing pre-term labor, intrauterine growth restriction, pre-eclampsia and/or a uterine disease or condition can also comprise assaying the activity of a COMT polypeptide obtained from the patient.

After a patient is identified as being at risk for developing pre-term labor, intrauterine growth restriction, and/or pre-eclampsia, or as having an ovarian disease or condition or a uterine disease or condition, the methods of the present invention can also comprise treating the patient. The methods used to treat a patient include administering an effective amount of a COMT inhibitor to the patient. Alternatively and with respect to pre-term labor, intrauterine growth restriction and/or pre-eclampsia conditions, the treatment can include, alone or in combination with the administration of a COMT inhibitor, bed rest or administering a compositions comprising an antibiotic, a tocolytic drug, a non-estradiol anti-inflammatory drug and/or a calcium channel blocker. The tocolytic drug can include ritoderine and/or terbtuline. The non-estradiol anti-inflammatory drug can include indomethacine. The calcium channel blocker can be nifedipine. Non-limiting examples of the antibiotics that can be used with this invention include penicillin, erythromycin, ampicillin or clindamycin. Additional antibiotics that are known in the art can also be used with this invention.

As for genitourinary conditions, including uterine diseases or conditions, the treatment can include, alone or in combination with the administration of a COMT inhibitor, radiation therapy, chemotherapy, hormonal therapy, immunotherapy, surgery, gene therapy and hyperthermia. In particular embodiments, the treatment comprises hormonal therapy, the hormonal therapy comprising administering a COMT inhibitor to the patient.

Concentrations of a COMT inhibitor can be about, at least about, or at most about, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 mg/kg or more, or any range derivable therein. In certain embodiments, the concentration is between about 30 to about 150 mg/kg.

In certain embodiments, more than one COMT inhibitor is given to a patient. In other embodiments, at least two COMT inhibitors are administered.

In a particular aspect of this invention, there is provided a method of preventing or treating a uterine tumor in a patient comprising administering an effective amount of a COMT inhibitor to the patient in need of the inhibitor, wherein the patient has a first allele encoding a valine at position 158 of a COMT polypeptide. The patient in need of the inhibitor can also have a second allele encoding a valine or methionine at position 158 of a COMT polypeptide.

Another particular embodiment of the present invention provides a method of preventing or treating pre-term labor in a patient comprising administering an effective amount of a COMT inhibitor to the patient in need of the inhibitor, wherein the patient has a first allele encoding a valine at position 158 of a COMT polypeptide. The patient in need of the inhibitor can also have a second allele encoding a valine or methionine at position 158 of a COMT polypeptide.

The present invention also provides for methods of identifying a candidate inhibitor of a genitourinary disorder comprising: (a) providing a COMT polypeptide and a non-methylated catechol-estrogen; (b) contacting a candidate substance with the COMT polypeptide and the non-methylated catechol-estrogen; and (c) determining the amount of methylated catechol-estrogen, wherein a decrease in methylated catechol-estrogen, as compared to the amount of methylated catechol-estrogen in the absence of the candidate substance, identifies the candidate substance as a candidate inhibitor of a genitourinary disorder. In specific embodiments, the genitourinary disorder is a uterine disease or condition. This method can further comprise (d) introducing the candidate inhibitor to a uterine cell or to an ovarian cell; and, (e) comparing COMT activity or expression in the cell to the COMT activity or expression in a cell not introduced with the candidate inhibitor. It is contemplated that COMT activity can be determined based on the level of COMT expression, and vice versa.

Another method contemplated by the present invention includes a method of identifying a candidate inhibitor of a uterine disease or condition comprising: (a) contacting a uterine cell expressing a COMT polypeptide with a candidate substance; and (b) comparing the activity or expression level of COMT polypeptide in the uterine cell contacted with the candidate substance to the activity or expression level of COMT polypeptide in a uterine cell not contacted with the candidate substance, wherein a decrease in activity or expression level in the cell contacted with the candidate substance compared to the cell not contacted with the candidate substances identifies the candidate substance as a candidate inhibitor of a uterine disease or condition. The uterine cell can be a leiomyoma cell. Different COMT polypeptides may be employed, such as the polypeptides reflecting the different polymorphisms at position 158. In some embodiments, a candidate substance is contacted with a uterine cell expressing one type of COMT polypeptide, such as one with a valine at position 158, and the candidate substance is contacted with a second uterine cell expressing a different COMT polypeptide, such as one with a methionine at position 158, and the activity or expression level of that particular COMT evaluated and/or compared to the level in the other COMT polypeptide.

Other screening methods for COMT inhibitors can involve assays described in the examples to test whether a particular candidate substance has the same or similar effect as the COMT inhibitor used in the Examples, under similar conditions. Thus, any experiment shown in the Examples is contemplated for use in methods of the invention, including screening methods or methods to evaluate a substance.

The terms "inhibiting," "reducing" or "prevention," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Any embodiment discussed with respect to a particular genitourinary disorder can be applied or implemented with respect to a different genitourinary disorder. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Effect of 2-OHE2 and CI on Luciferase activity in ELT3 cells infected with AdERE-Luc. "uM" means µM.

Figure 11:
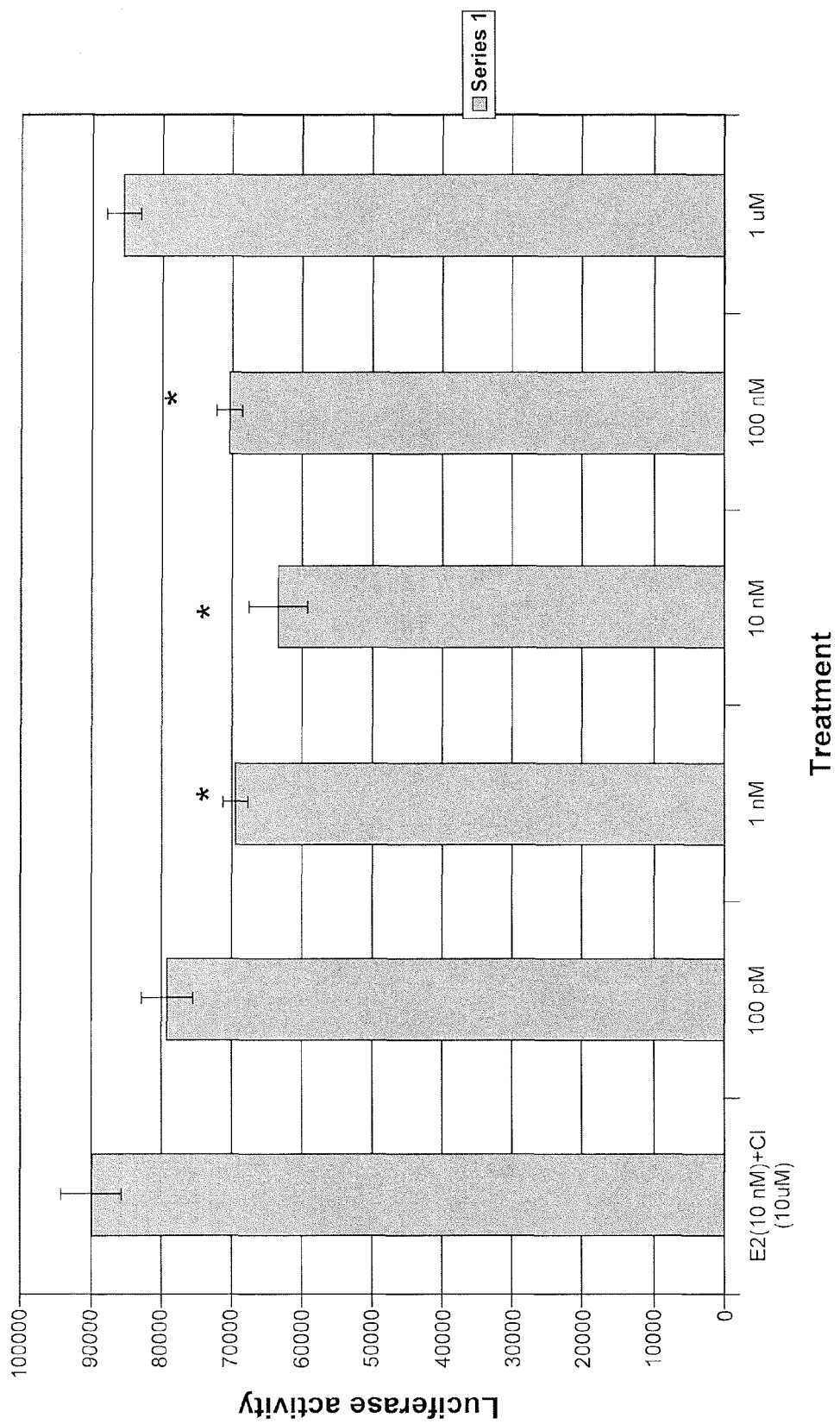

FIG. 11. Effect of 2-OHE2 and CI (+10 nM E2) on Luciferase activity in ELT3 cells infected with AdERE-Luc. "uM" means µM.

Figure 12:
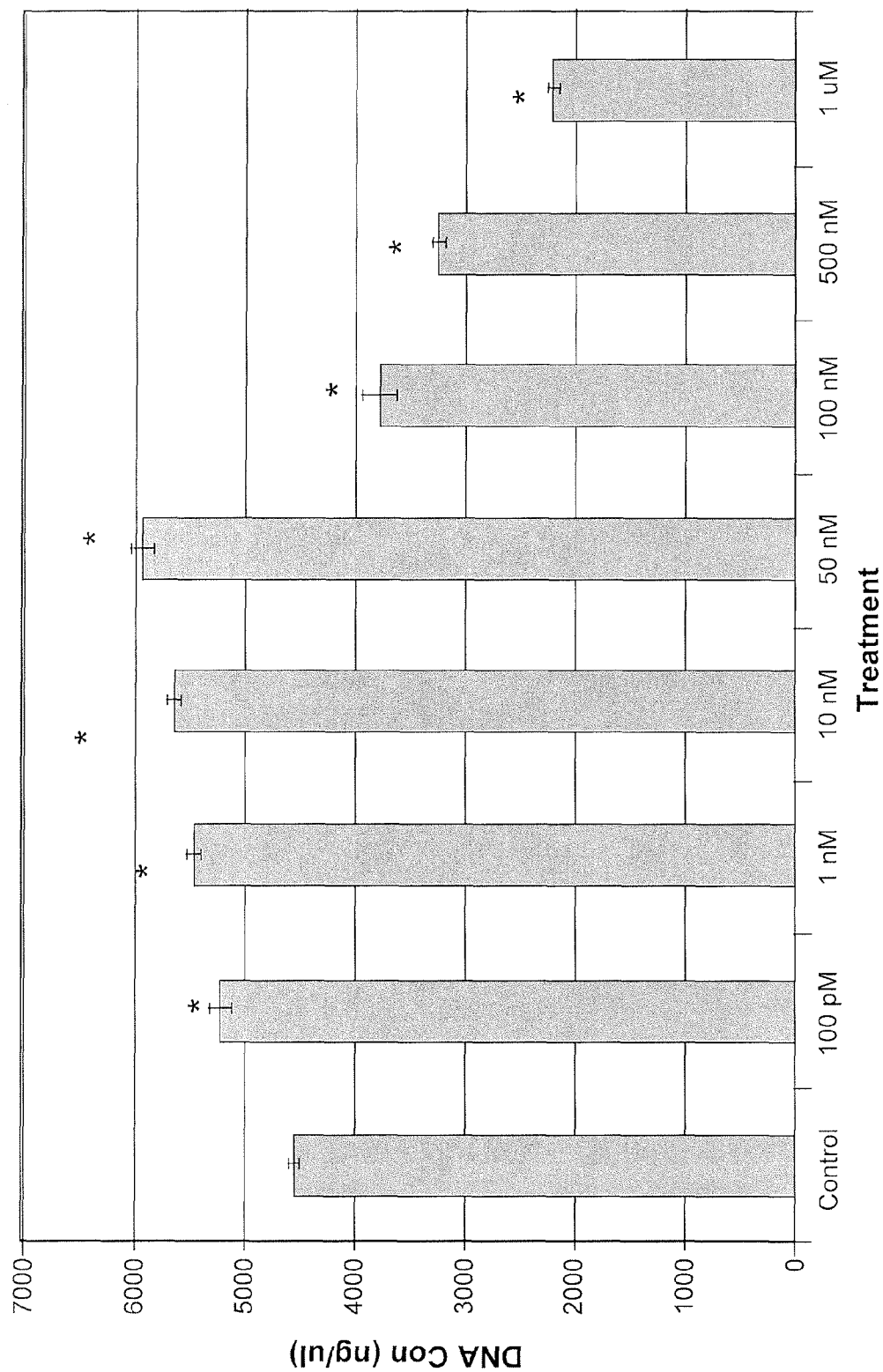

FIG. 12. Effect of 2-methoxyestradiol on ELT3 cell proliferation. "uM" means µM.

Figure 13:
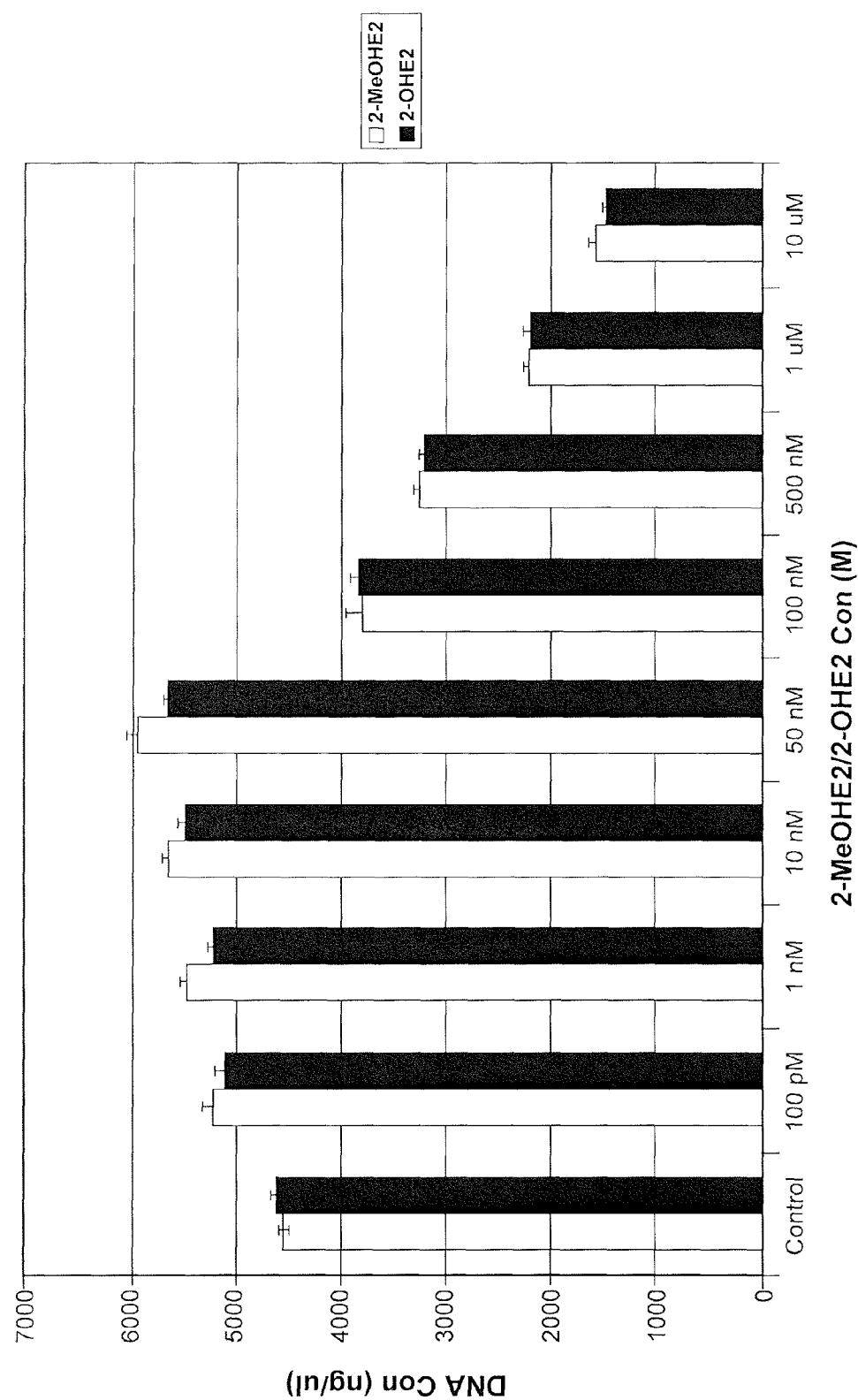

FIG. 13. Effect of 2-MeOHE2 and 2-OHE2 on the proliferation of ELT3 cells. "uM" means µM.

DESCRIPTION OF ILLUSTRATIVE EMBODIMENTS

Uterine diseases and conditions such as leiomyomas are common in women. Uterine leiomyomas, for example, arise from the uterine myometrium and are the most common tumor of the female reproductive tract. Uterine leiomyomas occur in 25-50% of all women, although estimates from autopsy specimens in which microscopic lesions were assessed histologically place the incidence as high as 77% of reproductive age women (Cramer and Patel, 1990). They are the number one cause of hysterectomy in reproductive age women, accounting for over 200,000 of these surgeries annually in the US alone (Buttram and Reiter; 1981) at an estimated cost of 1.7 billion dollars per year (McLachlan et al., 1986). In addition, they are a significant cause of pelvic pain, menorrhagia, abnormal uterine bleeding, infertility and complications of pregnancy (Rice et al., 1989; Carlson et al., 1994; Rowe et al., 1999; Coronado et al., 2000 and Kjerulff et al., 2000).

Similarly, preterm labor is a major factor in perinatal morbidity and mortality in the United States. It can result in preterm birth, a complication that affects 8 to 10 percent of births in the United States each year. (Weismiller, 1999) Although survival rates have increased while morbidity has decreased in recent years, the actual rate of premature births remains consistent. (Weismiller, 1999). In fact, the health care costs associated with preterm labor and preterm birth are over $3 billion per year. (Weismiller, 1999).

The inventor now discloses novel methods of treating and preventing the development of preterm labor and/or uterine diseases and conditions. Also disclosed are novel methods of diagnosing and identifying people at risk of developing such medical conditions. These and other aspects of the invention are described in greater detail below.

I. UTERINE LEIOMYOMA

The risk of developing a uterine leiomyoma increases with age during the premenopausal years but tumors typically regress and/or become asymptomatic with the onset of menopause (Cramer and Patel, 1990; Kjerulff, 1996). In addition to menopausal status, several other hormone-associated risk factors for uterine leiomyomas have been identified. Obesity, age at menarche, and unopposed estrogen exposure have been linked to an increased risk for uterine leiomyoma. In contrast, cigarette smoking, use of oral contraceptives and parity have been identified as protective factors (Marshall et al., 1997; Ross et al., 1986; Kjerulff et al., 1996; Parazzini et al., 1996; Marshall et al., 1998; and Chiaffarino et al., 1999). In the case of pregnancy, the risk of uterine leiomyoma in parous women is approximately half that of nulliparous women, and the risk of developing this disease decrease significantly with increased number of pregnancies (Ross et al., 1986; Kjerulff et al., 1996; Parazzini et al., 1996; and Marshall et al., 1998).

The hormonal responsiveness of uterine leiomyoma is supported by both clinical data and in vivo and in vitro experimental studies. In the clinic, standard adjuvant therapy involves the use of GnRH agonists in conjunction with myomectomy or hysterectomy. GnRH agonists induce a hypoestrogenic hormonal milieu similar to menopause by interrupting the hypothalamic-pituitary axis. Although these drugs can reduce the overall size of leiomyomas, as well as clinical symptoms, a course of treatment as short as 6 months induces a significant loss of bone mineral density in women that is only partially reversible (Dawood et al., 1989 and Lethaby et al, 2001). Numerous studies have established that leiomyomas express estrogen (ER) and progesterone (PR) receptors and laboratory studies with primary cultures of leiomyoma-derived cells indicate that they are responsive to steroid hormones (Brandon et al., 1995 and Wilson et al., 1996). Rodent leiomyoma cells derived from the Eker rat model for this disease proliferate in response to estrogen in culture, and this response can be inhibited by estrogen antagonists such as ICI 182780, tamoxifen and raloxifene (Howe et al., 1995; Fuchs-Young et al., 1996). There is also good evidence that a hyperestrogenic milieu within the tumors themselves may contribute to tumor growth (Pollow et al., 1978). Endometrial glandular hyperplasia is seen at the margins of submucosal leiomyomas, consistent with the existence of a localized hyperestrogenic environment in close proximity to the tumor (Deligdish and Loewnthal, 1970). More recently, investigations into the expression of estrogen metabolizing enzymes in leiomyomas have revealed that compared to normal myometrium, leiomyomas preferentially metabolize 17β-estradiol to the 4-hydroxy rather than the 2-hydroxy metabolite, the 4-hydroxy metabolite being associated with tumorgenesis in the breast and reproductive tract (Zhu and Conney, 1998). In addition, an elevated transcriptional response to estrogen in leiomyomas suggests that these tumors may have an increased responsiveness or are hypersensitive to estrogen stimulation Andersen et al., 1995.

It is known that symptomatic uterine leiomyomas are more common in black women than in white women (Zaloudek and Hendrickson, 2002). Observers from the nineteenth and first half of the twentieth century reported on the higher incidence of uterine leiomyomas in dark-skinned races (Balloch, 1984; Witherspoon and Butler, 1934 and Torpin et al., 1942). The existence of these ethnic differences was reconfirmed recently (Kjerulff et al., 1993; Wilcox et al., 1994 and Marshall et al., 1997). The molecular basis of this ethnic variation is completely unknown. A recent report found no difference in estrogen receptor alpha (ER-α) levels in myometrium of black and white women with ULM (Al-Hendy and Luxon, 2002).

Recently, some attempts to expose leiomyoma to the powerful technique of gene arrays have been reported (Al-Hendy and Luxon, 2002; Tsibris et al., 2002; and Chegini et al., 2003). Although there is some evidence that somatic genetic factors may influence the development of leiomyomas, e.g. non-random cytogenetic changes, as yet these studies have not led to the identification of any gene with proven involvement in the etiology of leiomyomas (Chegini et al., 2003; Patrikis et al., 2003 and Massart et al., 2001). Few recent studies reported as association between estrogen receptor alpha (ER-α) polymorphism and uterine leiomyomas (Massart et al., 2001; Hsieh et al., 2003 and Kitawaki et al., 2001) in Italian, Taiwan, and Japanese women respectively. No such studies are available from North American patients with uterine leiomyomas.

II. CATECHOL-O-METHYLTRANSFERASE (COMT)

Catechol-O-methyltransferase (COMT) is ubiquitous enzyme that catalyses the S-adenosyl-L-methionine dependent methyl conjugation of the hydroxyl groups of catechol estrogens and catecholamine neurotransmitters thereby leading to inactivation (Axelrod and Tomchick, 1958). A common genetic polymorphism, G→A transition at codon 158 resulting in a valine-to-methionine substitution, is associated with thermal instability and a four fold decrease in enzymatic activity (Lachman et al., 1996). The genotypes designated in relation to the predicated enzymatic activity of the protein are high ($COMT^{Val/Val}$), intermediate ($COMT^{Val/Met}$), and low ($COMT^{Met/Met}$) (Lachman et al., 1996).

The gene encoding for the COMT polypeptide encodes both the soluble COMT (S-comt) and the membrane-bound COMT (MB-COMT) by using separate promoters. SEQ. ID. NO:1 refers to the nucleic acid sequence for human COMT. SEQ. ID. NO:2 refers to the amino acid sequence for human COMT. The rat nucleic acid and amino acid sequences for COMT can be obtained by referring to GenBank Accession No. NM012531 (the rat nucleic acid and amino acid sequences are specifically incorporated into this specification by reference).

COMT is found in invertebrates and vertebrates (Reenila, 1999). In mammals, COMT is distributed in a variety of tissues, including the liver, kidney, glands, muscle tissue, adipose tissue, blood cells (Reenila, 1999). Rat and human S-COMT polypeptides each contain 221 amino acids. The molecular weights of these polypeptides are 25 kDa and 26 kDa, respectively (Reenila, 1999).

III. COMT INHIBITORS

A particular aspect of the present invention includes the use of COMT inhibitors to prevent and/or treat a patients having or at risk of developing pre-term labor, intrauterine growth restriction, pre-eclampsia and/or a uterine disease or condition. It is contemplated by the inventors that all types of COMT inhibitors, including compositions and drugs comprising COMT inhibitors, can be used as part of this invention.

Non-limiting examples of COMT inhibitors that can be used with the present invention include, for example, molecules containing a 5-nitrocatechol moiety such as entacapone, nitecapone, tocapone and Ro 41-0960. A non-limiting example of drugs and compositions comprising a COMT inhibitor that can be used with this invention include Tasmar® and Comtan®.

IV. POLYMORPHISMS

In some embodiments, the present invention concerns identifying polymorphisms in COMT, correlating genotype to phenotype, and then identifying such polymorphisms in patients who have or will be given a COMT inhibitor. Thus, a particular aspect of the present invention involves assays for identifying polymorphisms and other nucleic acid detection methods.

A. Nucleic Acid Detection

Nucleic acids can be used as probes or primers for embodiments involving nucleic acid hybridization. They can also be used in diagnostic or screening methods of the present invention. Detection of nucleic acids encoding COMT, as well as nucleic acids involved in the expression or stability of COMT polypeptides or transcripts, are encompassed by the invention.

General methods of nucleic acid detection methods are provided below, followed by specific examples employed for the identification of polymorphisms, including single nucleotide polymorphisms (SNPs).

1. Hybridization

The use of a probe or primer of between 13 and 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

2. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO: 1 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™)

which is described in detail in U.S. Pat. Nos. 4,683,195, 4,683,202 and 4,800,159, and in Innis et al., 1988.

A reverse transcriptase PCR™ amplification procedure may be performed to quantify the amount of mRNA amplified. Methods of reverse transcribing RNA into cDNA are well known (see Sambrook et al., 2001). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846, 709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; PCT Application WO 88/10315). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 discloses a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1994; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721 which discloses an apparatus and method for the automated electrophoresis and transfer of nucleic acids. The apparatus permits electrophoresis and blotting without external manipulation of the gel and is ideally suited to carrying out methods according to the present invention.

4. Screening Assays to Detect a Polymorphism

Several methods have been developed to screen and detect polymorphisms in genomic DNA, cDNA and/or RNA samples. Such methods include the direct or indirect sequencing of target regions, the use of restriction enzymes where the respective alleles of the site create or destroy a restriction site, the use of allele-specific hybridization probes, the use of antibodies that are specific for the proteins encoded by the different alleles of the polymorphism, denaturing gradient gel electrophoresis ("DGGE"), restriction fragment length polymorphism analysis ("RFLP"), chemical or enzymatic cleavage methods, single-strand conformation polymorphism analysis ("SSCP") and other methods well known in the art. Some screening methods are explained in more detail below.

i DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes. (Mullis et al., 1986; European Patent Appln. 50,424; European Patent Appln. 84,796, European Patent Application 258,017, European Patent Appln. 237,362; European Patent Appln. 201,184; U.S. Pat. No. 4,683,202; U.S. Pat. No. 4,582,788; and U.S. Pat. No. 4,683,194).

ii RNase Cleavage

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

iii Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'-to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

iv Microsequencing Methods

Several other primer-guided nucleotide incorporation procedures for assaying polymorphic sites in DNA have been described (Komher et al., 1989; Sokolov 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1993).

v Extension in Solution

French Patent 2,650,840 and PCT Application No. WO91/02087 discuss a solution-based method for determining the identity of the nucleotide of a polymorphic site. According to these methods, a primer, complementary to allelic sequences immediately 3'-to a polymorphic site is used. The identity of the nucleotide of that site is determined using labeled dideoxynucleotide derivatives which are incorporated at the end of the primer if complementary to the nucleotide of the polymorphic site.

vi Genetic Bit Analysis or Solid-Phase Extension

PCT Appln. No. WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

vii Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR™ are also described (Nickerson et al., 1990). Here PCR™ is used to achieve the exponential amplification of target DNA, which is then detected using the OLA.

viii Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

5. SNP Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLP s are been widely used in human and animal genetic analyses.

Another class of polymorphisms are generated by the replacement of a single nucleotide. Such single nucleotide polymorphisms (SNPs) rarely result in changes in a restriction endonuclease site. Thus, SNPs are rarely detectable restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset Alzheimer disease etc.

In context of the present invention, polymorphic mutations that affect the activity and/or levels of the COMT gene products can be determined by a series of screening methods. One set of screening methods is aimed at identifying SNPs that affect the activity and/or level of the COMT gene products in in vitro assays. The other set of screening methods will then be performed to screen an individual for the occurrence of the SNPs identified above. To do this, a sample (such as blood or other bodily fluid or tissue sample) will be taken from a patient for genotype analysis. The presence or absence of SNPs will determine the ability of the screened individuals to metabolize estrogen. According to methods provided by the invention, these results will be used to determine if a patient is in need of a COMT inhibitor or to adjust and/or alter the dose of a COMT inhibitor to be administered to a patient.

SNPs can be the result of deletions, point mutations and insertions and in general any single base alteration, whatever the cause, can result in a SNP. The greater frequency of SNPs means that they can be more readily identified than the other classes of polymorphisms. The greater uniformity of their distribution permits the identification of SNPs "nearer" to a particular trait of interest. The combined effect of these two attributes makes SNPs extremely valuable. For example, if a particular trait (e.g., decreased catabolism of estrogen) reflects a mutation at a particular locus, then any polymorphism that is linked to the particular locus can be used to predict the probability that an individual will be exhibit that trait.

V. PROTEINACEOUS COMPOUNDS AND COMPOSITIONS

In certain embodiments, the present invention concerns the use of compositions or methods comprising at least one proteinaceous molecule. The proteinaceous molecule can be, for example, COMT, CE or an inhibitor of COMT. In particular aspects, the proteinaceous molecule can be used in a pharmaceutical composition for the delivery of a therapeutic agent. In other embodiments, COMT and/or CE may be used as part of a screening assay for COMT modulators.

As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may be, be at least, or be at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 or greater contiguous amino molecule residues, and any range derivable therein. Such lengths are specifically contemplated for SEQ ID NO:2, and any other polypeptide described herein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

A. Protein Synthesis

The proteinaceous molecules that can be used in the present invention, e.g., COMT and CE, can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), Houghten et al. (1985). In some embodiments, peptide synthesis is contemplated by using automated peptide synthesis machines, such as those available from Applied Biosystems (Foster City, Calif.).

Longer peptides or polypeptides also may be prepared by recombinant means, e.g., by the expression of a nucleic acid sequence encoding a peptide or polypeptide, e.g. COMT and CE, in an in vitro translation system or in a living cell, as described in detail below. In certain embodiments of this invention, a nucleic acid encoding COMT or CE protein or peptides thereof is comprised in, for example, a vector in a recombinant cell. The nucleic acid may be expressed to produce a COMT or CE protein or peptides thereof. The COMT or CE protein or peptides thereof may be secreted from the cell, or comprised as part of or within the cell.

B. Purification of Proteins

It may be desirable to purify COMT, CE or modulators of COMT activity polypeptides, heterologous peptides or variants thereof. Protein purification techniques are well known to those of skill in the art. Examples of such techniques include Polyacrylamide Gel Electrophoresis, High Performance Liquid Chromatography (HPLC), Gel chromatography or Molecular Sieve Chromatography and Affinity Chromatography.

HPLC is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography can also be used to purify proteins of the present invention. Gel chromatography is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography can also be used in the purification of proteinaceous material. Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature.).

The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

VI. NUCLEIC ACIDS

The present invention concerns nucleic acids. In some cases, a nucleic acid is evaluated to determine whether a patient has a particular polymorphism, however, in other embodiments, a nucleic acid molecule is a COMT inhibitor.

A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product. In addition to the COMT gene and the CE gene, other regulatory regions such as enhancers for COMT and CE are contemplated as nucleic acids for use with compositions and methods of the claimed invention.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

The term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecules encoding COMT or another therapeutic polypeptide, probes and primers may comprise a contiguous nucleic acid sequence of the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences may be identical or complementary to SEQ ID NOS:1, 3 or 4.

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NOS:1, 3 or 4 are contemplated. Sequences that are essentially the same as those set forth in SEQ ID NOS:1, 3 or 4 may also be functionally defined as sequences that are capable of hybridizing to a nucleic acid segment or the complement of SEQ ID NOS:1, 3 or 4 under standard conditions.

A. Preparation of Nucleic Acids

A nucleic acid encoding COMT or CE may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032 or via deoxynucleoside H-phosphonate intermediates as described by Froehler et al., 1986 and U.S. Pat. No. 5,705,629. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244.

A non-limiting example of an enzymatically produced nucleic acid include one produced by enzymes in amplification reactions such as PCR™ (see for example, U.S. Pat. No. 4,683,202 and U.S. Pat. No. 4,682,195), or the synthesis of an oligonucleotide described in U.S. Pat. No. 5,645,897.

A non-limiting example of a biologically produced nucleic acid includes a recombinant nucleic acid produced (i.e., replicated) in a living cell, such as a recombinant DNA vector replicated in bacteria (see for example, Sambrook et al. 2001).

B. Purification of Nucleic Acids

A nucleic acid may be purified on polyacrylamide gels, cesium chloride centrifugation gradients, or by any other means known to one of ordinary skill in the art (see for example, Sambrook et al., 2001). In preferred aspects, a nucleic acid is a pharmacologically acceptable nucleic acid. Pharmacologically acceptable compositions are known to those of skill in the art, and are described herein.

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

C. Nucleic Acid Segments

In certain embodiments, the nucleic acid is a nucleic acid segment. As used herein, the term "nucleic acid segment," are fragments of a nucleic acid, such as, for a non-limiting example, those that encode only part of a peptide or polypeptide sequence. Thus, a "nucleic acid segment" may comprise any part of a gene sequence, including from about 2 nucleotides to the full length of a peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

D. Nucleic Acid Complements

The present invention also encompasses a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarily rules. As used herein "another nucleic acid" may refer to a separate molecule or a spatial separated sequence of the same molecule. In preferred embodiments, a complement is an antisense nucleic acid used to reduce expression (e.g., translation) of a RNA transcript in vivo.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some antisense embodiments, completely complementary nucleic acids are preferred.

E. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236 and which can be bought, for example, under the name MAXBAC® 2.0 from INVITROGEN® and BACPACK™ BACULOVIRUS EXPRESSION SYSTEM from CLONTECH®.

Other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

F. Viral Vectors

There are a number of ways in which expression vectors may be introduced into cells. In certain embodiments of the invention, the expression vector comprises a virus or engineered vector derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

The retroviruses are a group of single-stranded RNA viruses characterized by an ability to convert their RNA to double-stranded DNA in infected cells; they can also be used as vectors. Lentiviruses can also be used as vector. Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

In some embodiments, the vector is HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

G. Array Preparation

The present invention concerns diagnostic methods, which can be achieved using arrays, which are ordered macroarrays or microarrays of nucleic acid molecules (probes) that can detect a COMT-encoding sequence and that are positioned on a support material in a spatially separated organization. Alternatively, an array can be employed to identify or characterize a COMT inhibitor that is a nucleic acid.

A variety of different array devices in which a plurality of distinct nucleic acid probes are stably associated with the surface of a solid support are known to those of skill in the art. Useful substrates for arrays include nylon, glass and silicon Such arrays may vary in a number of different ways, including average probe length, sequence or types of probes, nature of bond between the probe and the array surface, e.g. covalent or non-covalent, and the like. The labeling and screening methods of the present invention and the arrays are not limited in its utility with respect to any parameter except that the probes detect COMT sequences or COMT inhibitors; consequently, methods and compositions may be used with a variety of different types of arrays.

Representative methods and apparatus for preparing a microarray have been described, for example, in U.S. Pat. Nos. 5,143,854; 5,202,231; 5,242,974; 5,288,644; 5,324,633; 5,384,261; 5,405,783; 5,412,087; 5,424,186; 5,429,807; 5,432,049; 5,436,327; 5,445,934; 5,468,613; 5,470,710; 5,472,672; 5,492,806; 5,525,464; 5,503,980; 5,510,270; 5,525,464; 5,527,681; 5,529,756; 5,532,128; 5,545,531; 5,547,839; 5,554,501; 5,556,752; 5,561,071; 5,571,639; 5,580,726; 5,580,732; 5,593,839; 5,599,695; 5,599,672; 5,610;287; 5,624,711; 5,631,134; 5,639,603; 5,654,413; 5,658,734; 5,661,028; 5,665,547; 5,667,972; 5,695,940; 5,700,637; 5,744,305; 5,800,992; 5,807,522; 5,830,645; 5,837,196; 5,871,928; 5,847,219; 5,876,932; 5,919,626; 6,004,755; 6,087,102; 6,368,799; 6,383,749; 6,617,112; 6,638,717; 6,720,138, as well as WO 93/17126; WO 95/11995; WO 95/21265; WO 95/21944; WO 95/35505; WO 96/31622; WO 97/10365; WO 97/27317; WO 99/35505; WO 09923256; WO 09936760; WO0138580; WO 0168255; WO 03020898; WO 03040410; WO 03053586; WO 03087297; WO 03091426; WO03100012; WO 04020085; WO 04027093; EP 373 203; EP 785 280; EP 799 897 and UK 8 803 000; the disclosures of which are all herein incorporated by reference.

It is contemplated that the arrays can be high density arrays, such that they contain 100 or more different probes. It is contemplated that they may contain 1000, 16,000, 65,000, 250,000 or 1,000,000 or more different probes. The probes can be directed to targets in one or more different organisms. The oligonucleotide probes range from 5 to 50, 5 to 45, 10 to 40, or 15 to 40 nucleotides in length in some embodiments. In certain embodiments, the oligonucleotide probes are 20 to 25 nucleotides in length.

The location and sequence of each different probe sequence in the array are generally known. Moreover, the large number of different probes can occupy a relatively small area providing a high density array having a probe density of generally greater than about 60, 100, 600, 1000, 5,000, 10,000, 40,000, 100,000, or 400,000 different oligonucleotide probes per $cm^2$. The surface area of the array can be about or less than about 1, 1.6, 2, 3, 4, 5, 6, 7, 8, 9, or 10 $cm^2$.

Moreover, a person of ordinary skill in the art could readily analyze data generated using an array. Such protocols are disclosed above, and include information found in WO 9743450; WO 03023058; WO 03022421; WO 03029485; WO 03067217; WO 03066906; WO 03076928; WO 03093810; WO 03100448A1, all of which are specifically incorporated by reference.

Use of a biochip is also contemplated, which involves the hybridization of a labeled molecule or pool of molecules to the targets immobilized on the biochip.

VII. PHARMACEUTICAL COMPOSITION AND ROUTES OF ADMINISTRATION

One embodiment of this invention includes methods of treating or preventing uterine diseases, uterine conditions or pre-term labor by the delivery of a COMT inhibitor to a patient in need. Uterine diseases or conditions that can be treated in the present invention include, but are not limited to, leiomyomas, adenomyosis, endometriosis, endometrila hyperplasia or cancer and any other hyperproliferative diseases that may be treated by altering the activity of catechol-estrogen.

An effective amount of the pharmaceutical composition, generally, is defined as that amount sufficient to detectably and repeatedly to ameliorate, reduce, minimize or limit the extent of the disease or its symptoms. More rigorous definitions may apply, including elimination, eradication or cure of disease.

Preferably, patients will have adequate bone marrow function (defined as a peripheral absolute granulocyte count of >2,000/mm$^3$ and a platelet count of 100,000/mm$^3$), adequate liver function (bilirubin<1.5 mg/dl) and adequate renal function (creatinine<1.5 mg/dl).

A. Pharmaceutical Compositions

Pharmaceutical compositions of the present invention include COMT inhibitors. The phrases "pharmaceutical or pharmacologically acceptable" refers to molecular entities and compositions that do not produce an adverse, allergic or other untoward reaction when administered to an animal, such as, for example, a human. The preparation of a pharmaceutical composition including a COMT inhibitor will be known to those of skill in the art in light of the present disclosure, as exemplified by Remington's Pharmaceutical Sciences, 18th Ed. Mack Printing Company, 1990. Moreover, for animal (e.g., human) administration, it will be understood that preparations should meet sterility, pyrogenicity, general safety and purity standards as required by FDA Office of Biological Standards.

"Therapeutically effective amounts" are those amounts effective to produce beneficial results in the recipient animal or patient. Such amounts may be initially determined by reviewing the published literature, by conducting in vitro tests or by conducting metabolic studies in healthy experimental animals. Before use in a clinical setting, it may be beneficial to conduct confirmatory studies in an animal model, preferably a widely accepted animal model of the particular disease to be treated. Preferred animal models for use in certain embodiments are rodent models, which are preferred because they are economical to use and, particularly, because the results gained are widely accepted as predictive of clinical value.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990). Except insofar as any conventional carrier is incompatible with the active ingredient, its use in the therapeutic or pharmaceutical compositions is contemplated.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

Alternatively, a patient may be given $1 \times 10^{-5}$, $10^{-6}$, $10^{-6}$, $10^{-7}$, $10^{-8}$, $10^{-9}$, $10^{-10}$, $10^{-11}$, $10^{-12}$ M of a substance (or any range derivable therein), such as a COMT inhibitor, in a volume of 0.1 µl, 1.0 µl, 10 µl, 100 µl, 1 ml, 5 ml, 10 ml, 20 ml, 25 ml, 50 ml, 100 ml, 200 ml, 300 ml, 400 ml, 500 ml, or more (or any range derivable therein). Inhibitors may be administered 1, 2, 3, 4, 5, 6, 7, 8, 9, 10 or more times over a course of 1, 2, 3, 4, 5, 6, 7, 8, 9 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, 1, 2, 3, 4, 5, 6, 7, 8, 9, 10, 11, 12 months, or 1, 2, 3, 4, 5, 6, 7, 8, 9, 10 or more years on a regular or as needed basis.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The compositions of the present invention may comprise different types of carriers depending on whether it is to be administered in solid, liquid or aerosol form, and whether it need to be sterile for such routes of administration as injection.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments, the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments, the compositions are prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof, an excipient, such as, for example, dicalcium phosphate, mannitol, lactose, starch, magnesium stearate, sodium saccharine, cellulose, magnesium carbonate or combinations thereof, a disintegrating agent, such as, for example, corn starch, potato starch, alginic acid or combinations thereof, a lubricant, such as, for example, magnesium stearate; a sweetening agent, such as, for example, sucrose, lactose, saccharin or combinations thereof, a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition should be stable under the conditions of manufacture and storage, and preserved against the contaminating action of microorganisms, such as bacteria and fungi. It will be appreciated that exotoxin contamination should be kept minimally at a safe level, for example, less that 0.5 ng/mg protein.

B. Routes of Administration

The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrauterinely, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g. aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (Remington's, 1990).

VIII. COMBINATION THERAPIES

In order to increase the effectiveness of a treatment with the compositions of the present invention, such as a COMT inhibitor, it may be desirable to combine these compositions with other therapies effective in the treatment of pre-term labor or uterine diseases or conditions.

The compositions of the present invention can precede or follow the other agent treatment by intervals ranging from minutes to weeks. It is contemplated that one may administer both modalities within about 12-24 h of each other and, more preferably, within about 6-12 h of each other. In some situations, it may be desirable to extend the time period for treatment significantly, where several days (2, 3, 4, 5, 6 or 7) to several weeks (1, 2, 3, 4, 5, 6, 7 or 8) lapse between the respective administrations.

Various combinations may be employed where a compositions including a COMT inhibitor is "A" and the secondary agent, is "B":

```
A/B/A  B/A/B  B/B/A  A/A/B  A/B/B  B/A/A  A/B/B/B

B/A/B/B  B/B/B/A  B/B/A/B  A/A/B/B  A/B/A/B  A/B/B/A

B/B/A/A  B/A/B/A  B/A/A/B  A/A/A/B  B/A/A/A  A/B/A/A

A/A/B/A
```

A. Preterm Labor

Treatments that can be used in combination with the present invention to treat or prevent preterm labor include bed rest or a composition comprising an antibiotic, a tocolytic drug, a non-estradiol anti-inflammatory drug or a calcium channel blocker. Non-limiting examples of the tocolytic drugs that be used with this invention include ritodrine, terbutaline and/or magnesium sulfate. A non-limiting example of a non-estradiol anti-inflammatory drug is indomethacine. An example of a calcium channel blocker is nifedipine. Non-limiting examples of the antibiotics that can be used with this invention include penicillin, erythromycin, ampicillin or clindamycin.

B. Uterine and Ovarian Diseases or Conditions

Uterine diseases or conditions that can be treated with the present invention include various forms of uterine cancers and other hyperproliferative diseases. Moreover, the present invention applies to ovarian conditions and diseases as well. As such, treatments that can be used with the combination of the present invention include, e.g., anti-cancer agents or surgery, as well as other therapies commonly implemented with these conditions and diseases.

An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. Anti-cancer agents include biological agents (biotherapy), chemotherapy agents, and radiotherapy agents. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992).

In the context of the present invention, it is contemplated that COMT inhibitors could be used similarly in conjunction with chemotherapeutic, radiotherapeutic, gene therapy or other biological intervention, in addition to other pro-apoptotic or cell cycle regulating agents.

Administration of the compositions of the present invention to a patient will follow general protocols for the administration of the anti cancer therapy, taking into account the toxicity, if any, of the vector. It is expected that the treatment cycles would be repeated as necessary. It also is contemplated that various standard therapies, as well as surgical intervention, may be applied in combination with the described therapy.

1. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, immunotherapy and/or alternative therapies. Surgery can also be used as a treatment for other uterine or ovarian conditions or diseases.

Curative surgery includes resection in which all or part of cancerous or other relevant tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery), laparascopic surgery and harmonic scalpel surgery. It is further contemplated that the present invention may be used in conjunction with removal of superficial cancers, pre-cancers, or incidental amounts of normal tissue.

Upon excision of part of all of cancerous or otherwise affected cells, tissue, or tumor, a cavity may be formed in the body. Treatment may be accomplished by perfusion, direct injection or local application of the area with an additional therapy, such as an anticancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

2. Hormonal Therapy

Because fibroids grow in response to the female hormone estrogen, anti-estrogen hormones such as progesterone can shrink fibroids and may result in dramatic improvement in symptoms. Hormonal therapy is most useful in shrinking fibroids prior to surgery. The present invention therefore contemplates that hormonal therapy may be used with the present invention in treating and preventing uterine fibroids. Hormonal therapy may include a prescription for birth-control pills or other hormonal therapy, or the use of non-steroidal anti-inflammatory drugs (NSAIDs), such as ibuprofen or naproxen sodium. Aggressive hormonal therapy may employ Lupron. Lupron is a GNRH agonist that blocks ovarian estrogen production, is non-invasive, shrinks fibroids, and often improves symptoms. Other hormonal therapies contemplated with the present invention may include androgen, RU-486, and gestrinone. Additionally, prifenidone, a drug which blocks a chemical that helps fibroids grow may also be employed with the present invention.

One or more ovulation medications may also be administered as part of methods of the invention. Such ovulation medications include fertility drugs, which are widely used and well known, as well as birth control medications, which are also widely used and well known.

In particular embodiments, the second therapy can be 2-methoxy estradiol. It is specifically contemplated that this compound can be used with respect to leiomyomas.

3. Other Gene Therapy

Other gene therapies may also be combined with the present invention. These include but are not limited to apoptosis promoting molecules such as the Bcl-2 family members that function to promote cell death such as Bax, Bak, Bik, Bim, Bid, Bad, Mtd, Bcl-XS and Harakiri.

The caspases such as caspase-3, caspase-7 and caspase-9 are known to play critical roles as executioners of apoptosis. Therefore, caspase gene therapy may also be used in combination with the present invention to further promote cell death or tumor reduction. It is further contemplated that agents such as the TNF family members which are well known in the art, may also be employed to further promote cell death of tumor cells with the present invention. Tumor necrosis factor-related apoptosis—inducing ligand (TRAIL/Apo2L) which activates apoptosis in numerous cancers without toxicity to normal cells, and Fas-ligand are two such TNF family members. Other gene therapies that may also be employed with the present invention include tumor suppressor genes such as E1A gene and p53 which can function by inducing apoptosis and inhibiting metastasis.

The methods by which to employ other gene therapy with that of the present invention are well known to those of skill in the art. All of the above methods may further employ adenoviruses in targeting pathways that are involved in mediating cell kill in tumor cells.

4. Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy.

5. Radiotherapy

Other factors that cause DNA damage and have been used extensively in treating genitourinary tumors is further contemplated for used in the present invention in treating uterine tumors. These include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

6. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

IX. SCREENING ASSAYS

One important aspect of the present invention concerns assays for screening for potential COMT modulators that can be used in therapeutic applications. A COMT modulator refers to a compound that is able to increase or reduce effective COMT amount, expression, transcription, translation, or functional activity. The COMT modulator may be an agonist (inducer) or antagonist (inhibitor) of COMT. These assays may comprise random screening of large libraries of candidate substances; alternatively, the assays may be used to focus on particular classes of compounds selected with an eye towards structural attributes that are believed to make them more likely to modulate COMT.

By activity, it is meant that one may assay for a measurable effect on COMT enzyme activity. To identify a COMT modulator, one generally will determine the activity of COMT in the presence and absence of a candidate substance, wherein a modulator is defined as any substance that alters the amount or activity.

Assays may be conducted in cell free systems, in isolated cells, or in organisms including transgenic animals. It will, of course, be understood that all the screening methods of the present invention are useful in themselves notwithstanding the fact that effective candidates may not be found. The invention provides methods for screening for such candidates, not solely methods of finding them.

A. Candidate Substances

As used herein the term "candidate substance" refers to any molecule that may potentially inhibit or enhance the effective level of COMT activity or expression. A COMT inducer refers to a substance that increases the effective level of COMT activity or expression. A COMT inhibitor refers to a substance that decreases or reduces the effective level of COMT activity or expression. It is contemplated that the terms inhibitor and inducer are relative to conditions when the inhibitor or inducer is not present.

Candidate substances can include fragments or parts of naturally-occurring compounds or may be only found as active combinations of known compounds which are otherwise inactive. In one embodiment, the candidate substances are small molecules. In yet other embodiments, candidate substances may be synthetic or natural peptides. Examples of small molecules that may be screened include, but are not limited to, small organic molecules, peptides or fragments thereof, peptide-like molecules, nucleic acids, polypeptides, peptidomimetics, carbohydrates, lipids or other organic (carbon-containing) or inorganic molecules. Many pharmaceutical companies have extensive libraries of chemical and/or biological mixtures, often fungal, bacterial, or algal extracts, which can be screened with any of the assays of the invention to identify compounds that modulate COMT activity.

Alternatively, it is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds.

Other suitable candidate substances, compounds or modulators of the present invention will likely function to regulate, i.e., inhibit, including decrease, the expression or activity of COMT. Such candidate substances may include, but are not limited to, antisense molecules, ribozymes, siRNAs, antibodies (including single chain antibodies), other proteins that bind to COMT, small molecules, or organopharmaceuticals. Specifically contemplated is a molecule that mimics a COMT substrate and competes with its physiological substrate.

Candidate substances identified may then be tested in biochemical or biological assays to further identify COMT modulators. Functional assays can also be employed to characterize candidate substances. Moreover, one or more assays may be employed for quality control evaluations once a particular candidate substance is determined to be a COMT inhibitor for pharmaceutical formulation.

B. Rational Drug Design

The present invention also provides methods for developing drugs that modulate COMT activity or expression, particularly COMT inhibitors, that may be used to prevent or treat genitourinary disorders, including pre-term labor, intrauterine growth restriction, pre-eclampsia, ovarian diseases or conditions, and/or uterine diseases or conditions. One such method involves the prediction of the three dimensional structure of COMT or a substrate thereof using molecular modeling and computer stimulations. The resulting structure may then be used in docking studies to identify potential small molecule inhibitors that bind in the enzyme's active site with favorable binding energies.

As discussed above, candidate substances can be further tested or evaluated.

Rational drug design is therefore used to produce structural analogs of substrates for COMT. By creating such analogs, it is possible to fashion drugs having biological activity. In one approach, one would generate a three-dimensional structure for the COMT targets of the invention or a fragment thereof. This could be accomplished by X-ray crystallography, computer modeling or by a combination of both approaches.

It also is possible to use antibodies to ascertain the structure of a target compound modulator. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable compounds include antisense molecules, ribozymes, and antibodies (including single chain antibodies), each of which would be specific for the target molecule. Such compounds are described in greater detail elsewhere in this document. For example, an antisense molecule that bound to a translational or transcriptional start site, or splice junctions, would be ideal candidate modulators.

The term "drug" is intended to refer to a chemical entity, whether in the solid, liquid, or gaseous phase which is capable of providing a desired therapeutic effect when, administered to a subject. The term "drug" should be read to include synthetic compounds, natural products and macromolecular entities such as polypeptides, polynucleotides, or lipids and also small entities such as neurotransmitters, ligands, hormones or elemental compounds. The term "drug" is meant to refer to that compound whether it is in a crude mixture or purified and isolated.

C. Assay Formats to Screen for Inhibitors

The assays may be carried out at the protein or nucleic acid level. Such assays may find use in diagnostic applications for directing the treatment of a patient having, or at risk of developing, pre-term labor or uterine diseases or conditions. The assays may even provide insight as to the relative efficacy of a known COMT inhibitor.

1. In Vitro Assays

A straightforward assay to run is a binding assay. Binding of a molecule to a target may, in and of itself, be inhibitory, due to steric, allosteric or charge-charge interactions. This can be performed in solution or on a solid phase and can be utilized as a first round screen to rapidly eliminate certain compounds before moving into more sophisticated screening assays. The target may be either free in solution, fixed to a support, expressed in or on the surface of a cell. Examples of supports include nitrocellulose, a column or a gel. Either the target or the compound may be labeled, thereby permitting determining of binding. In another embodiment, the assay may measure the enhancement of binding of a target to a natural or artificial substrate or binding partner. Usually, the target will be the labeled species, decreasing the chance that the labeling will interfere with the binding moiety's function. One may measure the amount of free label versus bound label to determine binding or inhibition of binding. In other embodiments, binding may be determined by gel electrophoresis, gel filtration chromatography, fluorescence quenching, flow cytometry, elisa, solid phase immunoassay, or confocal microscopy.

A technique for high throughput screening of compounds is described in PCT Application WO 84/03564. In high throughput screening, large numbers of candidate inhibitory test compounds, which may be small molecules, natural substrates and ligands, or may be fragments or structural or functional mimetics thereof, are synthesized on a solid substrate, such as plastic pins or some other surface. Alternatively, purified target molecules can be coated directly onto plates or supports for use in drug screening techniques. Also, fusion proteins containing a reactive region (preferably a terminal region) may be used to link an active region of an enzyme to a solid phase, or support. The test compounds are reacted with the target molecule, and bound test compound is detected by various methods (see, e.g., Coligan et al., 1991).

2. In Vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter the condition to be treated, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as behavior, anemia, immune response, etc.

Treatment of these animals with candidate substances will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

3. Arrays

Hi-throughput assays, for example, arrays comprising a plurality of ligands arranged on a solid support, represent an important diagnostic tool provided by the invention. The use of arrays involves the placement and binding of nucleic acids, or another type of ligand having affinity for a molecule in a test sample, to known locations, termed sectors, on a solid support.

Arrays can be used, through hybridization of a test sample to the array, to determine the presence or absence of a given molecule in the sample. By including any additional other target nucleic acids or other types of ligands, potentially thousands of target molecules can be simultaneously screened for in a test sample. Many different methods for preparation of arrays comprising target substances arranged on solid supports are known to those of skill in the art and could be used in accordance with the invention. Specific methods for preparation of such arrays are disclosed in, for example, Affinity Techniques, Enzyme Purification: Jakoby and Wilchek, (1974) and Dunlap, (1974). Examples of other techniques which have been described for the attachment of test materials to arrays include the use of successive application of multiple layers of biotin, avidin, and extenders (U.S. Pat. No. 4,282,287); methods employing a photochemically active reagent and a coupling agent which attaches the photoreagent to the substrate (U.S. Pat. No. 4,542,102); use of polyacrylamide supports on which are immobilized oligonucleotides (PCT Patent Publication 90/07582); use of solid supports on which oligonucleotides are immobilized via a 5'-dithio linkage (PCT Patent Publication 91/00868); and through use of a photoactivateable derivative of biotin as the agent for immobilizing a biological polymer of interest onto a solid support (see U.S. Pat. No. 5,252,743; and PCT Patent Publication 91/07087). In the case of a solid support made of nitrocellulose or the like, standard techniques for UV-crosslinking may be of particular utility (Sambrook et al., 2001).

D. Specific Candidate Compounds

All of the candidate substances and compounds discussed can be used to screen for potential modulators of COMT activity and or expression. The following is a non-limiting detailed description of some of the many candidate compounds that is contemplated and can be used by the present invention.

1. Antibodies

The inventor contemplates the use of screening anti-COMT antibodies that are immunoreactive with COMT and modulate COMT activity. The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Harlow et al., 1988). Antibodies can be, and are not limited to, monoclonal, polyclonal, single chain, bi-specific, and/or humanized antibodies.

2. Antisense Molecules

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNAs, may be employed to inhibit gene transcription or translation or both within a host cell, either in vitro or in vivo, such as within a host animal, including a human subject.

3. siRNAs

An RNA molecule capable of mediating RNA interference in a cell is referred to as "siRNA." Elbashir et al. (2001) discovered a clever method to bypass the anti viral response and induce gene specific silencing in mammalian cells. Several 21-nucleotide dsRNAs with 2 nucleotide 3' overhangs were transfected into mammalian cells without inducing the antiviral response. The small dsRNA molecules (also referred to as "siRNA") were capable of inducing the specific suppression of target genes.

In the context of the present invention, siRNA directed against a COMT polypeptide are contemplated as COMT inhibitors. The siRNA can target a particular sequence because of a region of complementarity between the siRNA and the RNA transcript encoding the polypeptide whose expression will be decreased, inhibited, or eliminated.

An siRNA may be a double-stranded compound comprising two separate, but complementary strands of RNA or it may be a single RNA strand that has a region that self-hybridizes such that there is a double-stranded intramolecular region of 7 base pairs or longer (see Sui et al., 2002 and Brummelkamp et al., 2002 in which a single strand with a hairpin loop is used as a dsRNA for RNAi). In some cases, a double-stranded RNA molecule may be processed in the cell into different and separate siRNA molecules.

In some embodiments, the strand or strands of dsRNA are 100 bases (or base pairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or base pairs in length. A dsRNA that has a complementary region equal to or less than 30 base pairs (such as a single stranded hairpin RNA in which the stem or complementary portion is less than or equal to 30 base pairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 base pairs or fewer.

Methods of using siRNA to achieve gene silencing are discussed in WO 03/012052. Designing and testing siRNA for efficient inhibition of expression of a target polypeptide is a process well known to those skilled in the art. Also, kits are commercially available to those of skill in the art to make siRNA molecules, for example, Ambion sells several siRNA reagents.

4. Ribozymes

The use of COMT polypeptide-specific ribozymes is an embodiment of the present invention. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990; Sioud et al., 1992). Recently, it was reported that ribozymes elicited genetic changes in some cell lines to which they were applied; the altered genes included the oncogenes H-ras, c-fos and genes of HIV. Most of this work involved the modification of a target mRNA, based on a specific mutant codon that is cleaved by a specific ribozyme. In light of the information included in this specification and the knowledge of one of ordinary skill in the art, the preparation and use of additional ribozymes that are specifically targeted to a given gene will now be straightforward.

Several different ribozyme motifs have been described with RNA cleavage activity (reviewed in Symons, 1992). Examples that would be expected to function equivalently for the down regulation of Fortilin include sequences from the Group I self splicing introns including tobacco ringspot virus (Prody et al., 1986), avocado sunblotch viroid (Palukaitis et al., 1979; Symons, 1981), and Lucerne transient streak virus (Forster and Symons, 1987). Sequences from these and related viruses are referred to as hammerhead ribozymes based on a predicted folded secondary structure.

Other suitable ribozymes include sequences from RNase P with RNA cleavage activity (Yuan et al., 1992; Yuan and Altman, 1994), hairpin ribozyme structures (Berzal-Herranz et al., 1992; Chowrira et al., 1993) and hepatitis δ virus based ribozymes (Perrotta and Been, 1992). The general design and optimization of ribozyme directed RNA cleavage activity has been discussed in detail (Haseloff and Gerlach, 1988; Symons, 1992; Chowrira, et al., 1994; and Thompson, et al., 1995).

The other variable on ribozyme design is the selection of a cleavage site on a given target RNA. Ribozymes are targeted to a given sequence by virtue of annealing to a site by complimentary base pair interactions. Two stretches of homology are required for this targeting. These stretches of homologous sequences flank the catalytic ribozyme structure defined above. Each stretch of homologous sequence can vary in length from 7 to 15 nucleotides. The only requirement for defining the homologous sequences is that, on the target RNA, they are separated by a specific sequence which is the cleavage site. For hammerhead ribozymes, the cleavage site is a dinucleotide sequence on the target RNA, uracil (U) followed by either an adenine, cytosine or uracil (A, C or U; Perriman, et al., 1992; Thompson, et al., 1995). The frequency of this dinucleotide occurring in any given RNA is statistically 3 out of 16. Therefore, for a given target messenger RNA of 1000 bases, 187 dinucleotide cleavage sites are statistically possible.

Designing and testing ribozymes for efficient cleavage of a target RNA is a process well known to those skilled in the art. Examples of scientific methods for designing and testing ribozymes are described by Chowrira et al. (1994) and Lieber and Strauss (1995). The identification of operative and preferred sequences for use in debranching enzyme-targeted ribozymes is simply a matter of preparing and testing a given sequence, and is a routinely practiced "screening" method known to those of skill in the art.

5. Aptamers and Aptazymes

Other candidate COMT inhibitors include aptamers and aptazymes, which are synthetic nucleic acid ligands. The methods of the present invention may involve nucleic acids that modulate COMT polypeptides. Thus, in certain embodiments, a nucleic acid, may comprise or encode an aptamer. An "aptamer" as used herein refers to a nucleic acid that binds a target molecule through interactions or conformations other than those of nucleic acid annealing/hybridization described herein. Methods for making and modifying aptamers, and assaying the binding of an aptamer to a target molecule may be assayed or screened for by any mechanism known to those of skill in the art (see for example, U.S. Pat. Nos. 5,840,867, 5,792,613, 5,780,610, 5,756,291 and 5,582,981, Burgstaller et al., 2002.

X. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods for Example 2

Patients:

Subjects were classified as either black or white based on their statement of race at hospital admission for surgery and its agreement with skin color. Given the uncertainty of true ancestry, "black" and "white" were used to designate individuals of presumed African and Caucasian ancestry, respectively.

All women in this study had hysterectomy in order to ensure that control patients did not have any leiomyoma at the histological level. The hysterectomy was done abdominal, vaginal or laparoscopic. Test group had clinically, radiologically, surgically, and histologically documented leiomyoma. Control group women were having hysterectomy for other non-leiomyoma indications e.g. chronic pelvic pain without documented adenomyosis or endometriosis, recurrent cervical dysplasia, as part of management of benign ovarian masses, or abnormal uterine bleeding. They have histologically documented normal uteri. The inventor excluded women with uterine cancer, adenomyosis or endometriosis and recruited 263 healthy control women for this study (black 95, white 102, Hispanic 66) and 204 patient with uterine leiomyoma (black: 92, white: 68, hispanic: 44).

Genotyping:

DNA was extracted from peripheral blood samples and normal human myometrium (snap frozen in liquid nitrogen) as described in Abdel-Rahman et al., 1994. The following primers were used: 5'-CTC ATC ACC ATC GAG ATC AA-3' (forward) (SEQ ID NO:3) and 5'-CCA GGT CTG ACA ACG GGT CA-3' (reverse) (SEQ ID NO:4). PCR™ reactions contains 1 µl purified DNA (200-300 ng/ul), 1.5 units Taq DNA polymerase (Sigma, Saint Louis, Mo. USA), 10 mM Tris-HCL, 50 mM KCL, 1.5 mM $MgCl_2$, 0.2 mM dNTP in a DNA thermocycler Perkin Elmer Cetus, GeneAmp PCR system 9600 (Norwalk, Conn., USA).

| PCR ™ condition: | 95C 3' |
| --- | --- |
| 40 cycles: | 95C 1 |
|  | 54C 1' |
|  | 72C 1' |
|  | 72C 5' |
| PCR ™ product size: | 109 bp |

The Val and met alleles were discriminated by digesting the PCR™ product with 2 units of NlaIII (New England BioLabs) at 37° C. for overnight, following by 4.5% agarose gel electrophoresis. The val/val homozygotes (86 and 23 base pairs), met/met homozygotes (68 and 18 base pairs), and val/met heterozygotes (86, 68, 23 and 18 base pairs) were visualized by ethidium bromide staining.

Statistics:

The data are shown as mean±standard error of the mean (SEM). The statistical analysis was tested by analysis of variance (ANOVA) or paired t-test as indicated. A p value of less than 0.05 was considered statistically significant.

Example 2

Results

Demographic:

There was no statistical difference between patients and controls in age, weight, or parity. The distribution of ethnicity of the participants in both cases and control was not significantly different (data not shown).

Figure 1:
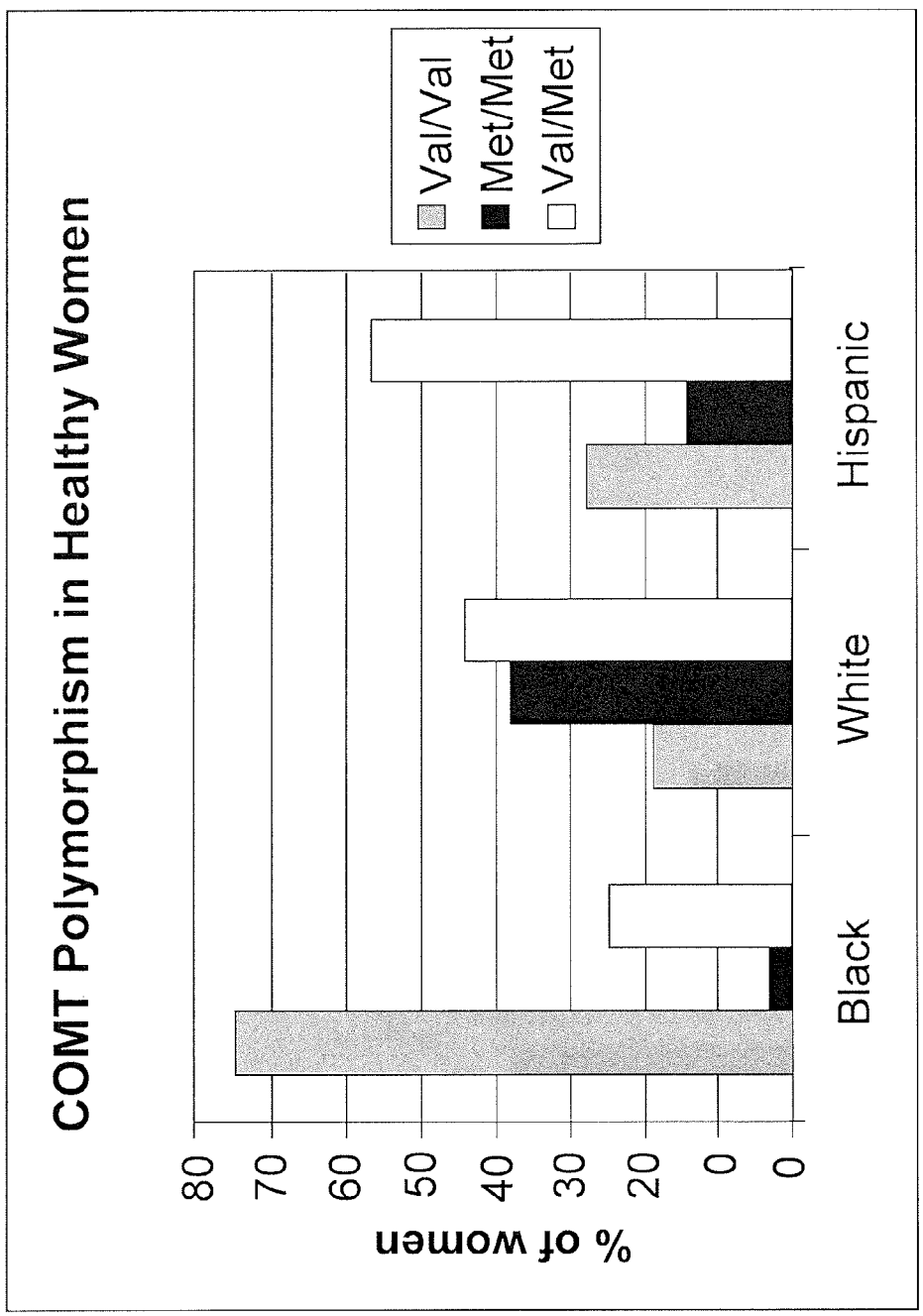
FIG. 1. Natural distribution of COMT variants in different ethnic groups. The VAL allele is more common in black women.

Natural Distribution of COMT Variants in Different Ethnic Groups (The VAL Allele is More Common in Black Women):

Strong epidemiological evidence documents a higher incidence of uterine leiomyoma in black women (Linde, 1997; Zaloudek and Hendrickson, 2002). This prompted the inventors to analyze the natural distribution of the two COMT variants in the healthy control sample first to assess if the VAL allele at least partially explains the higher incidence of leiomyoma in black women. In the control women, there was highly significant (P=0.0001) variation in the distribution of the Val and Met alleles between black and white women. As shown in FIG. 1, black women had high frequency of the Val/Val genotype (73%), and low frequency of the Met/Met genotype (2%), heterozygous Val/Met was 24%. In sharp contrast, in white women there was low frequency of Val/Val genotype (19%), and higher frequency of Met/Met genotype (38%), and heterozygous at 44%. Hispanic women had an intermediate frequency at Val/Val 28%, Met/Met 14%, and Val/Mat at 57%.

Figure 2:
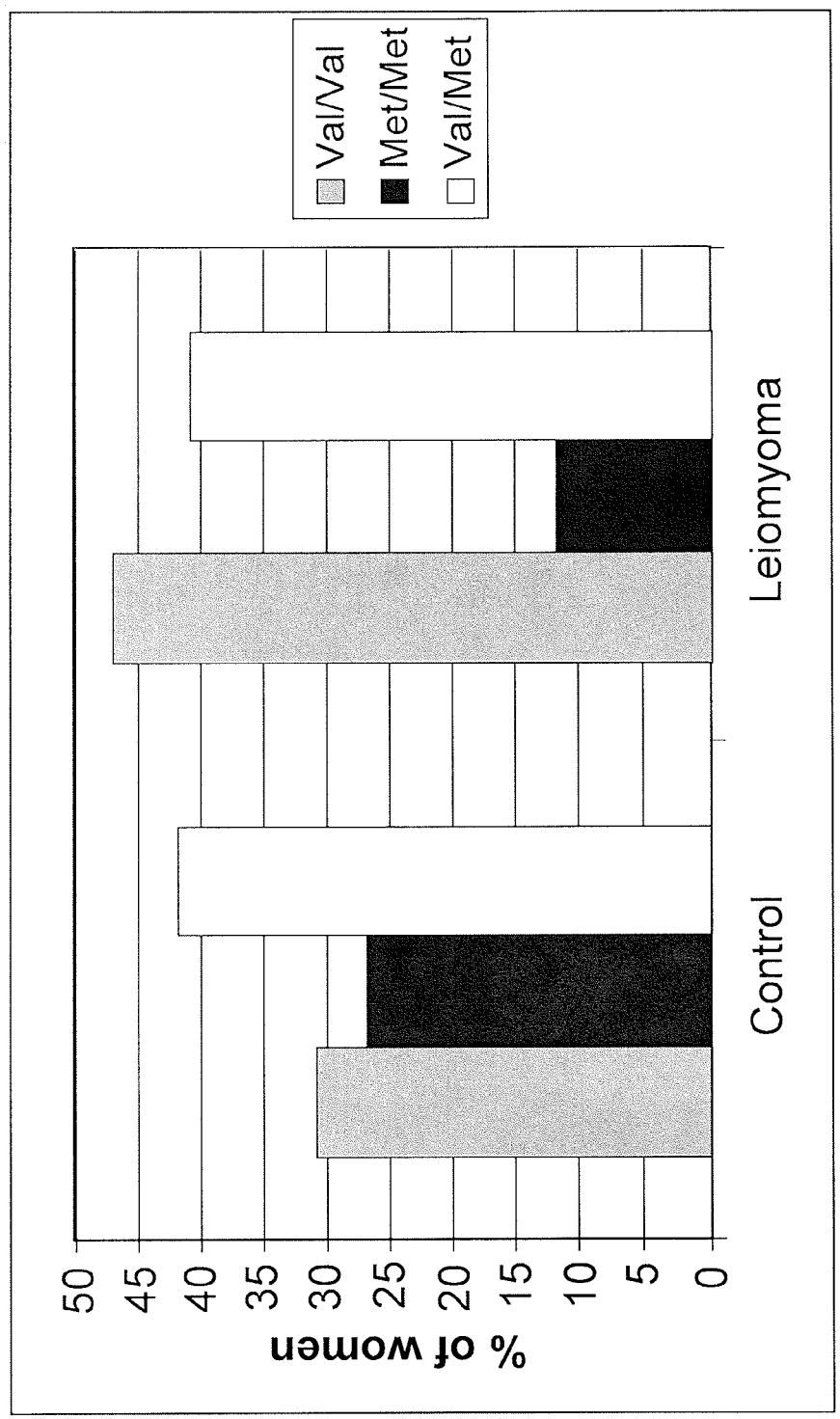
FIG. 2. The Val allele is associated with increased risk of leiomyoma.

The VAL Allele is Associated with Increased Risk of Leiomyoma:

The distribution of the Val and Met variants differed significantly between women with and without leiomyoma. FIG. 2 demonstrates that Val/Val genotype was highly represented in leiomyoma patients (47%) compared to 31% in control (P=0.0001). On the other hand, the homozygous Met/Met genotype was less represented in the leiomyoma patients (12%) versus 27% in control (P=0.0001). The heterozygous Val/Met genotype did not differ significantly between cases and controls at 41% versus 42% respectively (p=0.7). That significant difference was maintained also when cases and control women were compared within same ethnic group (data not shown).

Figure 3:
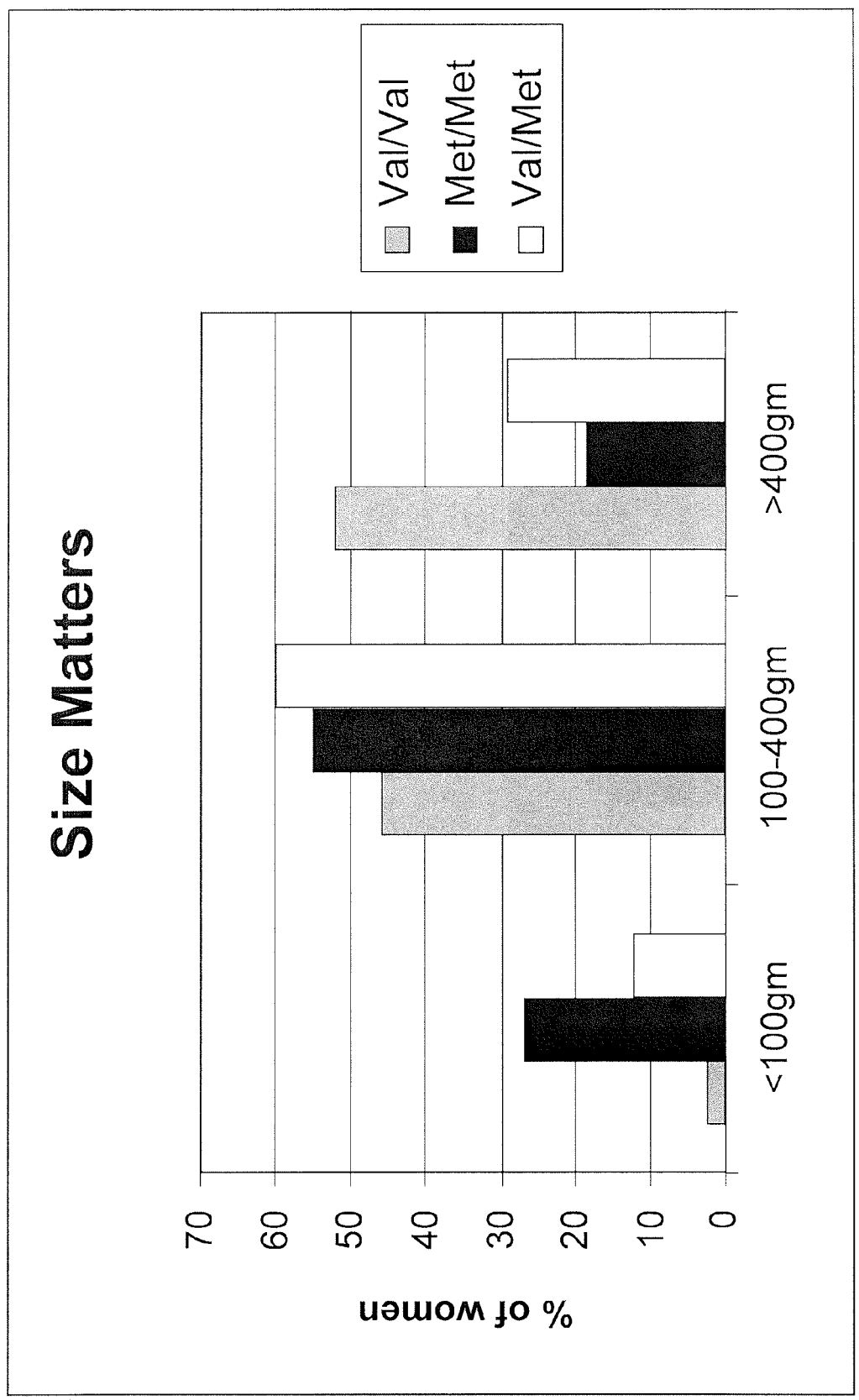
FIG. 3. The Val/Val variant is associated with severe disease.

Val/Val Variant is Associated with Severe Disease:

To further analyze the association of Val/Val and risk of uterine leiomyoma, the inventors assessed the potential connection between this genotype and advanced disease. Since uterine leiomyoma is a benign disease, the severity of the condition and magnitude of symptoms usually correlate to the size of the tumor and the uterus as a whole at the time of presentation. FIG. 3 shows the distribution of the two COMT genetic variants among women with different disease severity. Uteri volume <100 gm considered as mild disease, 100-400 gm as moderate disease and >400 gm (up to 6300 gm) as severe disease. The Met/Met genotype was highly represented in the mild disease group (uterine volume <100 gm, P=0.0001), while rare in the severe disease category. The Val/Val genotype had an opposite distribution with higher prevalence in the severe disease group (52%, P=0.0001).

Figure 4:
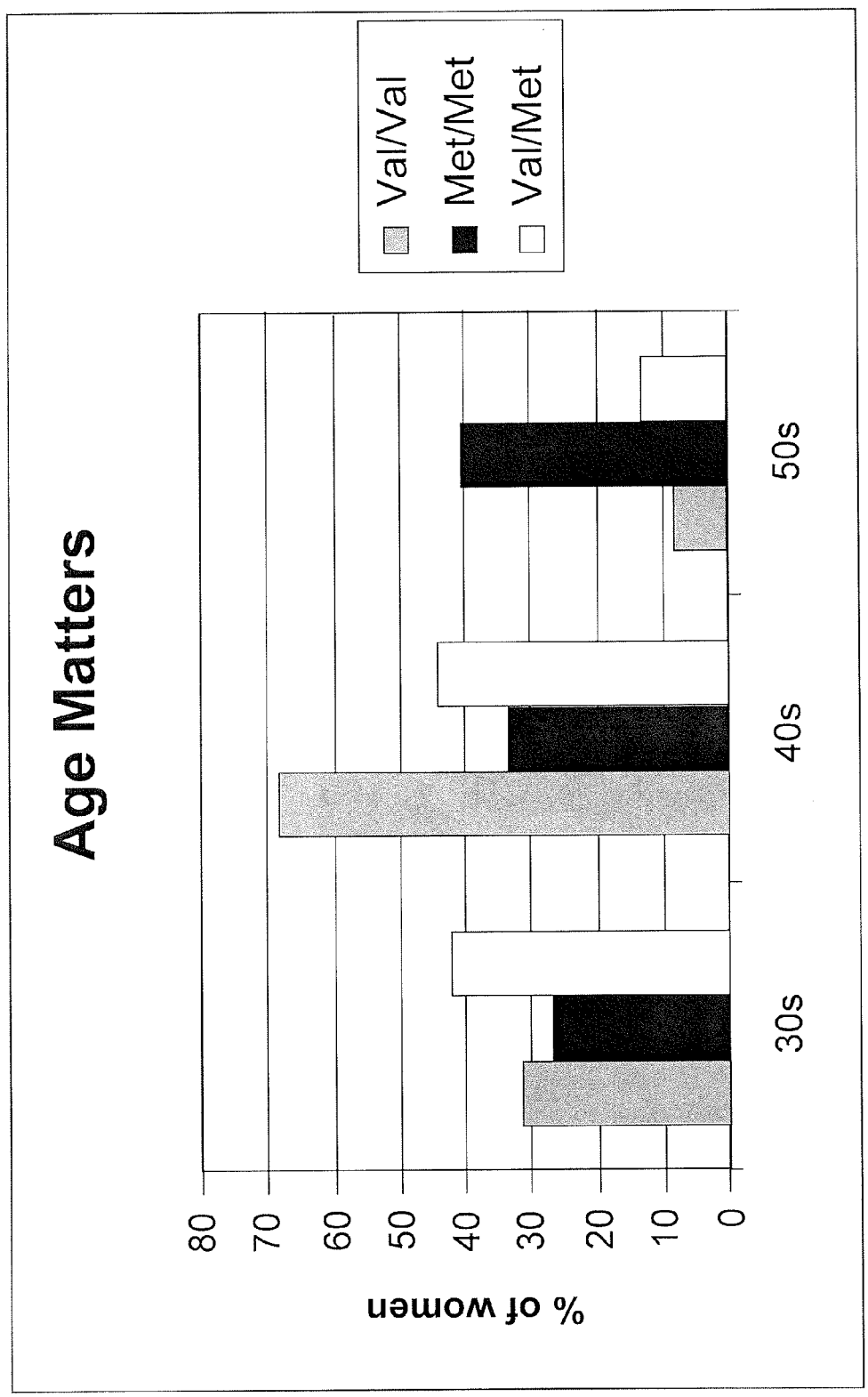
FIG. 4. The Val/Val variant is associated with early onset disease.

Val/Val Variant is Associated with Early Onset Disease:

If the Val/Val genotype was indeed associated with increased risk of leiomyoma, one would expect that women with this genotype would suffer not only from severe disease (as demonstrated above) but also from earlier onset of tumor and tumor-related symptoms. FIG. 4 demonstrates that most women with Val/Val genotype have their disease commence (and hence need hysterectomy) at least a decade earlier than their Met/Met counterparts (P=0.003).

Example 3

Discussion

The present invention identifies a correlation between the Val allele of the COMT gene and increased susceptibility to uterine diseases or conditions such as, for example, leiomyomas. Additionally, the inventor discovered that the Val allele was associated with earlier onset and more sever diseases.

The inventor also observed that homozygosity for the Val/Val variant is significantly more common in black and Hispanic patients with leiomyomas than in ethnic-matched controls. Homozygosity for the Val/Val variant increases susceptibility of the development of uterine diseases and conditions in a patient, such as the development of uterine leiomoymas.

Because 2-hydroxyestradiol works as antiestrogen in the uterus (Reddy et al., 1981), the high activity COMT (Val/Val variant) leads to lower levels of the antiestrogenic metabolites 2-hydroxyestradiol. This can lead to uncontrolled estrogenic effects of estradiol and subsequent development of uterine diseases and conditions, such as uterine tumors. This discovery can be used to diagnose, prevent and/or treat a patient having or at risk of developing a uterine disease or condition.

Example 4

Leiomyoma Tumorigenesis

Leiomyomas, especially in white women, occur in many patients with Met/Met genotype carriers. This shows that the underlying pathophysiology of leiomyomas in those cases are different than with patients having a Val/Val or a Val/Met genotype. This difference can be attributed to additional gene modifiers and/or environmental influences.

One of ordinary skill would be able to correlate COMT genotypes with expression of COMT mRNA and enzyme activity in tumor lesions. This can be done, for example, by comparing COMT mRNA expression and COMT enzymatic activity in leiomyoma cells with normal myometrium cells. Based on this correlation, it is possible to identify, prevent and/or treat a patient having or at risk of developing a uterine disease or condition, such as a leiomyoma. This discovery applies to patients having all genotype variations of the COMT gene, including Met/Met, Val/Met and Val/Val genotypes.

A model for uterine leiomyoma tumorgenesis is shown below:

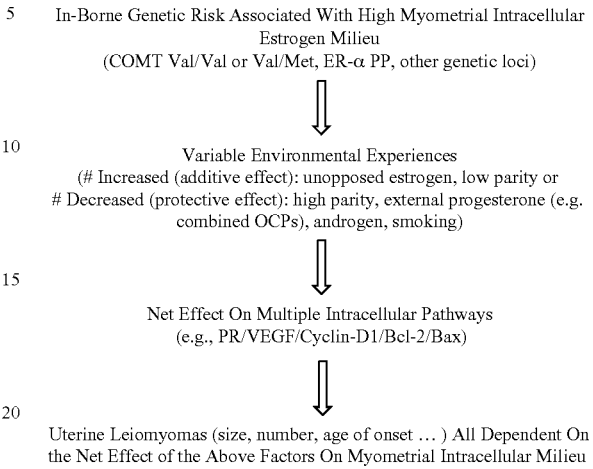

Example 5

Material and Methods for Example 6

Chemicals

β-Estradiol, 2-Hydroxyestradiol, and 2-Methoxyestradiol were purchased from Sigma Chemical Co ((St. Louis, Mo.). The antibiotics solution (containing 10,000 U/ml penicillin and 10 mg/ml streptomycin), trypsin-EDTA mixture (containing 0.25% trypsin and 0.02% EDTA), minimum essential medium (EMEM; phenol red-free), and calf bovine serum were purchased from Life Technology (Rockville, Md.). The Luciferase assay kit was purchased from Promega (WI, USA). Adenovirus ERE-Luciferase reporter vector was a gift from Dr. Lee EJ (Northwestern University, Chicago, Ill.) All other chemicals and biochemicals were the highest quality available from commercial sources.

Preparation of Solutions

The stock solution (10 mM) of β-Estradiol (E2), 2-Hydroxyestradiol (2-OHE2) and 2-Methoxyestradiol (2-MeOH E2) were freshly prepared in pure ethanol. The solution was then filtered with a 0.22 μm pore size Millex syringe filter. Serial dilutions were made and added to the cultured cells at the desired concentrations (10-5-10-10 M) for 2-OHE2 and 2-MeOHE2. For E2 (10-6-10-10 M) were used. COMT-inhibitor (R0 41-0960 from Sigma) was prepared in absolute ethanol (at concentrations of 10 mM) and added to the cultures at final concentration of 10 μM. The final concentration of ethanol in the cell culture medium was <0.01%.

Culture of ELT-3 Cells

The Eker rat tumor-derived ELT-3 uterine leiomyoma cells were grown in DMEM medium supplemented with 10% fetal bovine serum and 1% antibiotics (containing 100 U/ml penicillin and 100 μg/ml streptomycin. The cells were maintained in the 100 mm tissue culture dishes at 37° C. air with 5% $CO_2$ and 95% humidity. When experiments required the addition of exogenous compounds, cells were weaned by culturing for 48 h in phenol red-free medium containing 10% Charcoal-stripped fetal calf serum. For proliferation assays, cells were plated onto 24-well plates in DMEM at a density of 4000 cells/well. The cells allowed to attach overnight and then treated with E2 ($10^{-6}$ to $10^{-10}$ M) without COMT-inhibitor or with 10 μM of COMT-inhibitor, 2-OHE2 ($10^{-5}$ to $10^{-10}$ M) without COMT-I, or with 10 μM COMT-I, 2-OHE2, or 2-MeOHE2 ($10^{-5}$ to $10^{-10}$ M). Control cells were treated with medium containing 10 μl of absolute ethanol. After 48 hours, the cells were harvested for the proliferation assay. For western blot analysis, the cells were seeded in 100 mm plates at final density of $2 \times 10^6$ cells/plate. The cells were treated in 2-MeOHE2 in the same way as for the proliferation assay. Cells were harvested 48 hours after treatment and cell lysates were used for western blotting.

Cell Proliferation Assay

A fluorometric assay, implementing Hoechst 33258 (bis-benzimide), was used for DNA quantitation. ELT3 cells ($5 \times 10^3$ cells/well) were plated (described above). The cells were allowed to attach overnight at 37° C., and then the media were replaced with media containing the appropriate treatment. Control cells were treated with a 1:1000 dilution of absolute ethanol. The cells were incubated with the treatments for 48 hours, followed by cell lysis and DNA content determination using Hoechst dye solution (10 μl/100 ml distilled $H_2O$). Fluorescence was measured (DyNA Quant 200; Hoefer Pharmacia Biotech) after excitation at 365 nm and fluorescence at 458 nm. Calf thymus DNA was used as a standard to determine DNA concentration.

Western Blots

Immunoreactive proteins corresponding to VEGF, Cyclin D, Bcl-2, Bax, and β-actin were identified from total protein by western immunoblotting using specific monoclonal antibodies. The protein extraction and western blot techniques were essentially carried out as described previously (Al-Hendy et al., 2004). Briefly, after treatment of ELT3 cells with 2-MeOHE2 for 48 hours, the media were removed and the cells washed twice with cold PBS. Then, the cells were lysed in lysis buffer containing protease inhibitors (leupeptin, phenylmethylsulfonyl fluoride, and aprotinin) and incubated for 20 min at 4° C. After a 10-min spin at 10,000×g, the supernatant containing the total cell lysates were quantified using BCA Protein Assay Reagent (Pierce, Rockford, Ill.). Ten μg of total cell lysate were resolved by SDS-PAGE. Proteins were transferred overnight to polyvinylidene difluoride membrane and blocked for 1-2 h in 5% milk TBST or 2% milk PBST. A 1:300 dilution of primary antibodies recognizing VEGF, Cyclin D, Bcl2, or Bax (Santa Cruz Biotechnology, Santa Cruz, Calif.) was hybridized in % milk TBS-T for 2 h. The membranes were then washed once with Tris-buffered saline, followed by three washes with TBST and one final wash with Tris-buffered saline each for 5 minutes. Secondary antibodies conjugated to horseradish peroxidase (Santa Cruz Biotechnology) were hybridized for 1 h in 3% milk TBS-T. The wash sequence was the same as that stated previously. All hybridizations and washes were performed at room temperature. ECL western blotting detection reagents (Amersham Bioscience) was used for visualization. β-actin expression was used to assess consistent loading between samples. The expression level of target proteins was quantitated densitometrically and normalized using β-actin expression.

Cell Culture and Infection

Transfection of ELT3 cells with recombinant ERE-Luciferase adenovirus vector was achieved by maintaining ELT 3 cells as described above. For infection with estrogen response elements-luciferase reporter adenoviral vector (Ad ERE-Luc), the cells were allowed to grow to 60-70% confluence and then infected with Ad ERE-Luc vector at multiplicity of infection (MOI) of 100 plaque-forming units (PFU)/cell for two hours in infection medium containing 2% FCS and 1% penicillin/streptomycin. Then, the infection media were removed and replaced with regular media. The transduction efficiency of the adenoviral vectors in ELT3 cells was tested using Ad LacZ vector. β-Galactosidase expression was detected in 95-100% of ELT3 cells at 48 h after infection with Ad LacZ at a 100 PFU. Therefore, subsequent experiments were performed using similar amounts (100 PFU/cell) of recombinant Ad ERE-Luc vector.

ELT3 cells transfected with AdERE-Luc were treated with E2 and with or without COMT-I or with different concentrations of 2-OHE2 ($10^{-10}$ to $10^{-6}$ M) with or with out COMT-I (10 μM). After 48 h incubation with chemicals, cells were harvested with 100 μl of cell lysis buffer (Promega). Luciferase activity was determined using Luciferase Assay Kit (Promega) according to the manufacturer's instructions.

Example 5

Results

Mitogenic Effect of Estradiol on ELT3 Cells Proliferation

Figure 5:
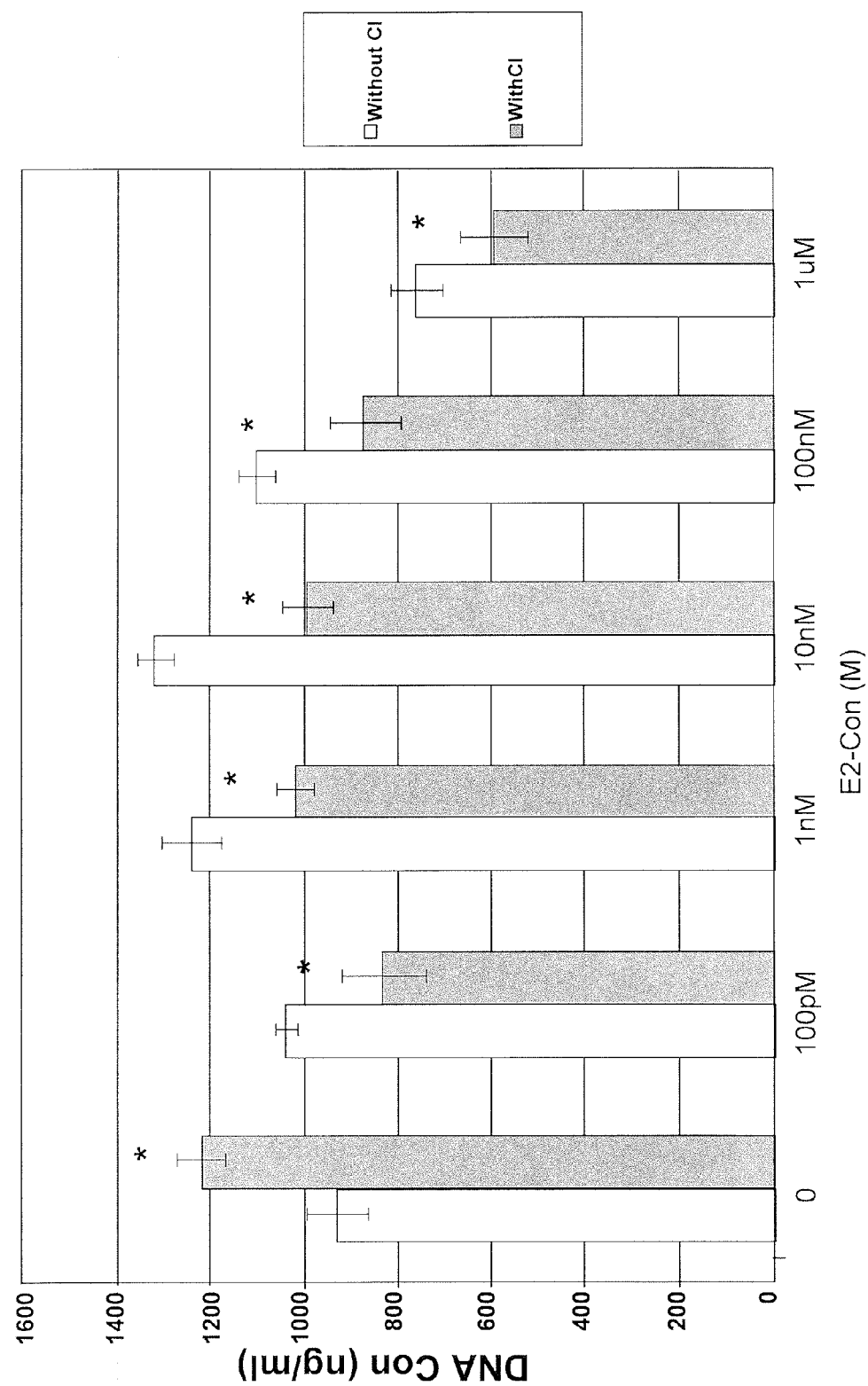
FIG. 5. Effect of Estrogen and COMT inhibitor (CI) on Rat Leiomyoma Cell Proliferation. ELT3 cells were grown with the indicated estradiol concentrations. COMT inhibitor was used at 10 µM concentration. * indicates significantly ($P<0.05$) different from the corresponding value for E2 alone. Results are mean±SEM from triplicate experiments. "uM" means µM.

To evaluate the effects of E2 alone or in combination with COMT inhibitor on the growth of ELT3 cells, the cells were treated with different concentrations of E2 ($10^{-10}$ to $10^{-6}$ M) with or without COMT inhibitor ($10^{-5}$ M). As shown in FIG. 5, E2 exhibits a concentration-dependent increase in ELT3 proliferation over the untreated control, with maximum effect observed at $10^{-8}$ M concentration. However, at higher concentrations ($10^{-7}$ to $10^{-6}$ M), the proliferative effect of E2 was limited or non-existing. As illustrated in FIG. 5, the addition of COMT inhibitor ($10^{-5}$ M) consistently inhibited the E2-induced cell proliferation on ELT3 cells. The antiproliferative effect of COMT inhibitor was statistically significant at all estrogen concentrations ($P<0.05$).

Effect of Estradiol and COMT Inhibitor on AdERE-Luc Reporter Vector Expression

Figure 6:
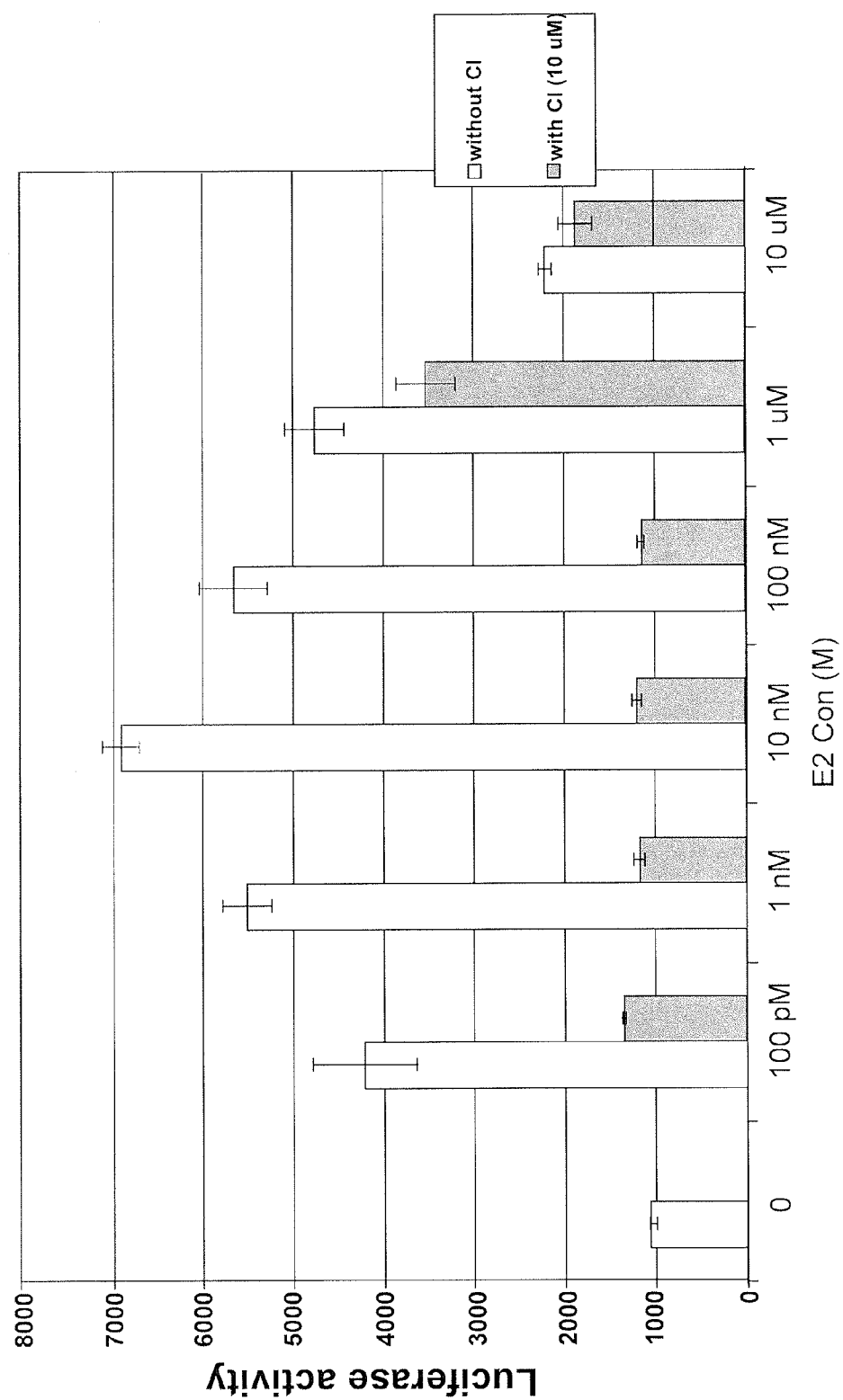
FIG. 6. Effect of Estradiol alone or in combination with CI (10 µM) on Luciferase activity in ELT3 cells infected with AdERE-Luc. "uM" means µM.

Next, the effect of E2 alone or in combination with COMT inhibitor on the estrogenic milieu in Leiomyoma ELT3 cells was evaluated using the AdERE-Luc reporter vector. In AdERE-Luc vector-transfected cells, E2 ($10^{-10}$ to $10^{-5}$ M) induced a concentration-dependent u-regulation of AdERE-Luciferase with the maximum effect (6-fold increase) was observed at $10^{-8}$ M (FIG. 6). Similar to the effect on cell proliferation, treatment with COMT inhibitor ($10^{-5}$ M) resulted in a significant down regulation of AdERE-luciferase compared to the treatment with E2 alone (FIG. 6). The effect of COMT inhibitor on E2-induced AdERE-Luciferase activity was significant ($P<0.05$) at the lower concentrations of E2 (10-10 to 10-7M). However, at the higher concentrations of E2 (10-6 and 10-5 M), the effect of COMT inhibitor on E2-induced AdERE-luciferase was less pronounced ($P=0.056$ and $P=0.17$, respectively).

Effect of 2-OHE2 and COMT Inhibitor on ELT3 Cells Proliferation

Figure 7:
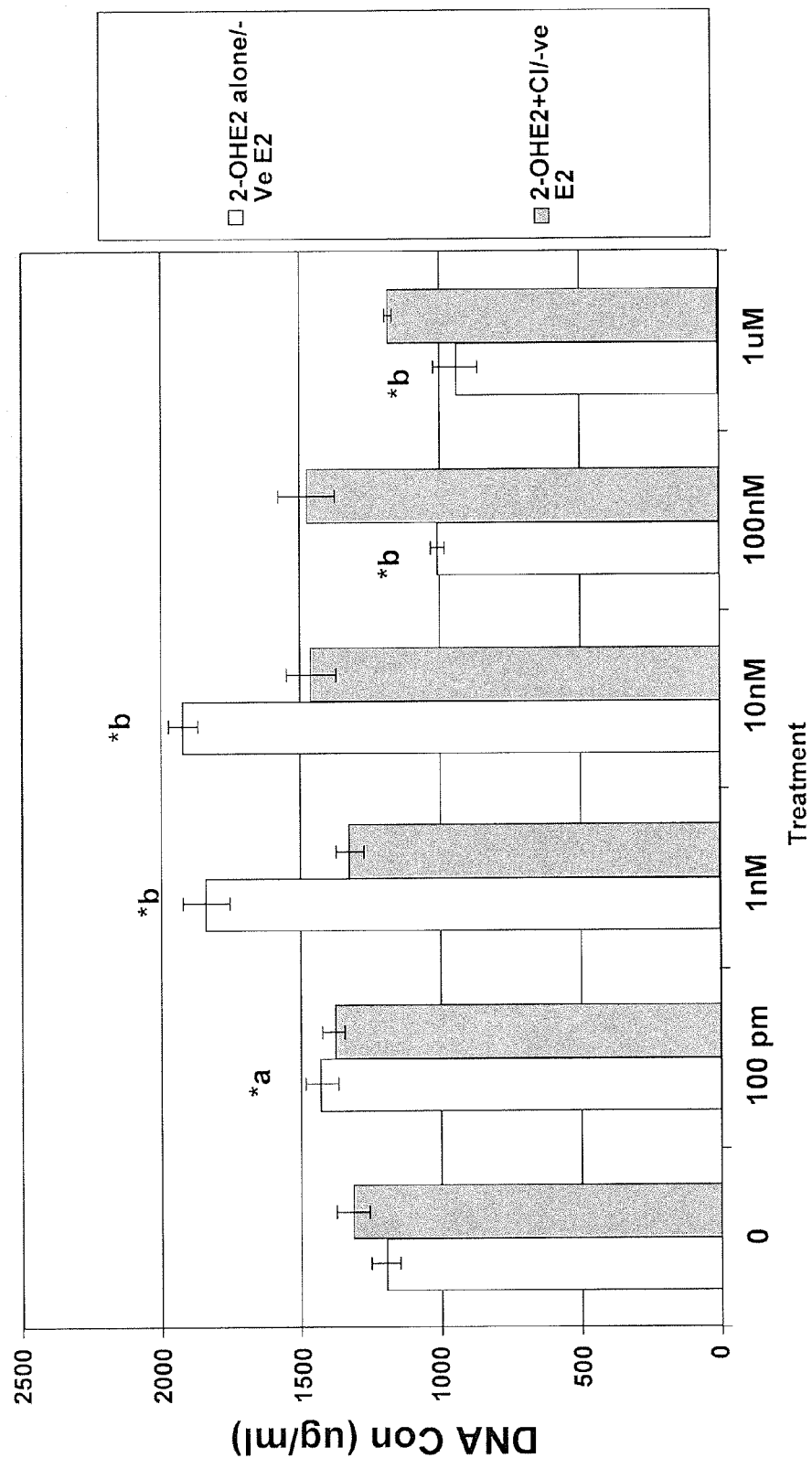
FIG. 7. Effect of 2-OHE2 alone or in combination with CI (no estrogen) on proliferation of ELT3 cells. *a indicates a level that is significantly different than the corresponding control ($p<0.05$). *b indicates a level that is significantly different than the control with 2-OHE2 alone. "uM" means µM.

Because the metabolites catechol estrogens are not inert metabolites, they exhibit a weak estrogen receptor agonist or partial antagonist (Gupta et al., 1998; Zhu and Conney, 1998), therefore, the effect of 2-OHE2 on ELT3 proliferation was investigated. As illustrated in FIG. 7, 2-OHE2 exhibited a paradoxical effect on ELT3 cells in proliferation assays. At low concentration levels ($10^{-10}$ to $10^{-9}$, or $10^{-8}$ M), 2-OHE2 has a significant mitogenic effect and the cell proliferation increased by 19%, 54%, 61%, respectively, from the control. However, at higher concentrations ($10^{-7}$ and $10^{-6}$ M), 2-OHE2 exhibited a remarkable antiproliferative effect with 16% and 21% reduction in cell proliferation, respectively, compared to the untreated control. These results were obtained in estrogen-free environment. Interestingly, in the presence of E2 ($10^{-8}$ M), the mitogenic effects of 2-OHE2

Figure 8:
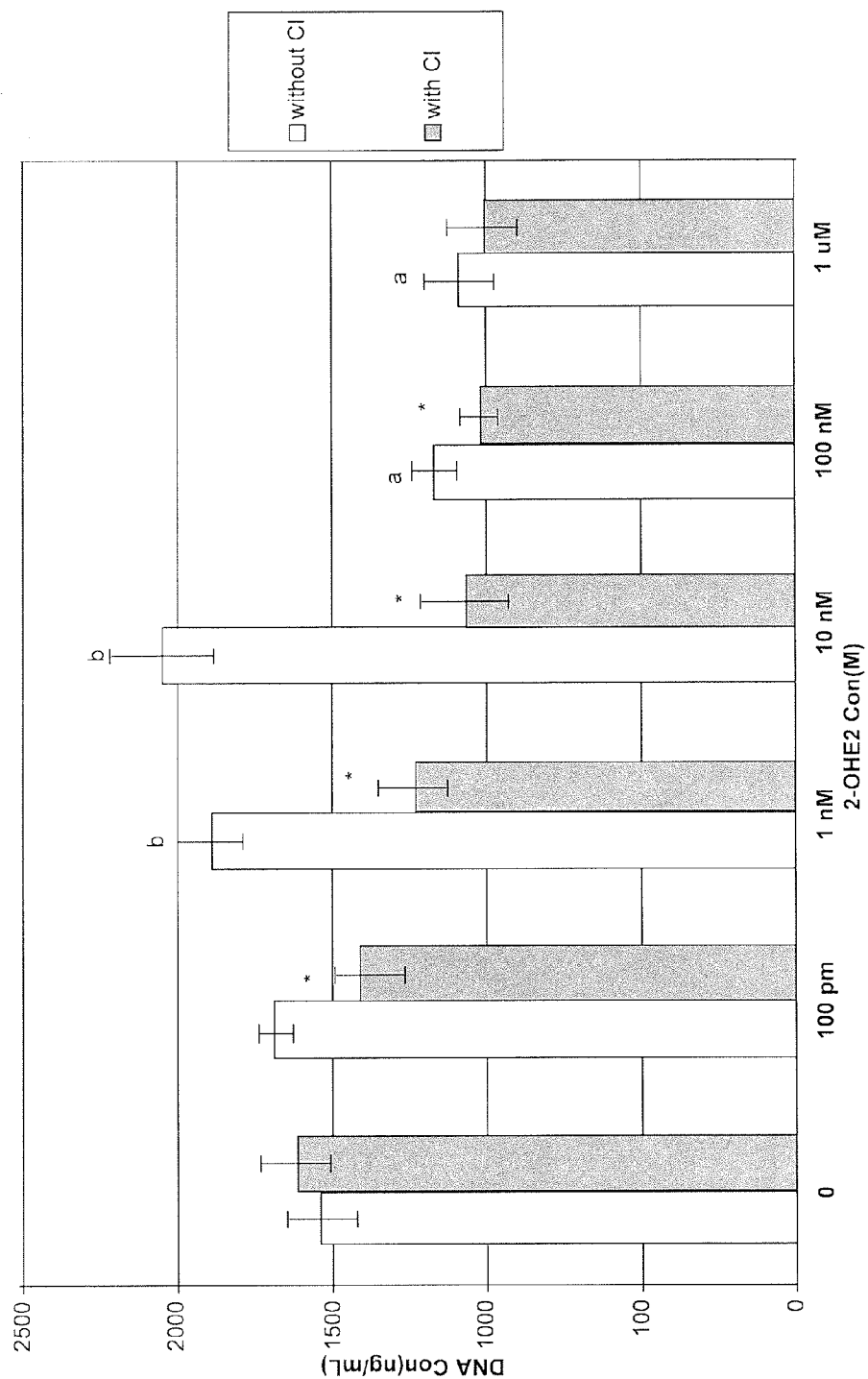
FIG. 8. Effect of 2-OHE2 alone and in combination with CI on ELT3 cell proliferation (+10 nM E2). * indicates significantly different than the corresponding control with 2-OHE2 alone. "a" indicates a significant level relative to the control. "b" indicates a level marginally significant relative to the control.

($10^{-10}$ to $10^{-9}$, or $10^{-8}$ M) were less evident compared to its effect in absence of E2. 2-OHE2 ($10^{-10}$ to $10^{-9}$, or $10^{-8}$ M) increased cell proliferation by 10%, 24%, and 33%, respectively E2 (FIG. 8).

Co-treatment with COMT inhibitor ($10^{-5}$ M) consistently antagonized the proliferative effect of low dose 2-OHE2 on ELT3 cells and augmented the antiproliferative effect of high dose 2-OHE2. The antiproliferative effect of COMT inhibitor was statistically significant at all 2-OHE2 concentrations ($P<0.05$).

Effect of 2-OHE2 and COMT Inhibitor on AdERE-Luc Reporter Vector Expression

Figure 9:
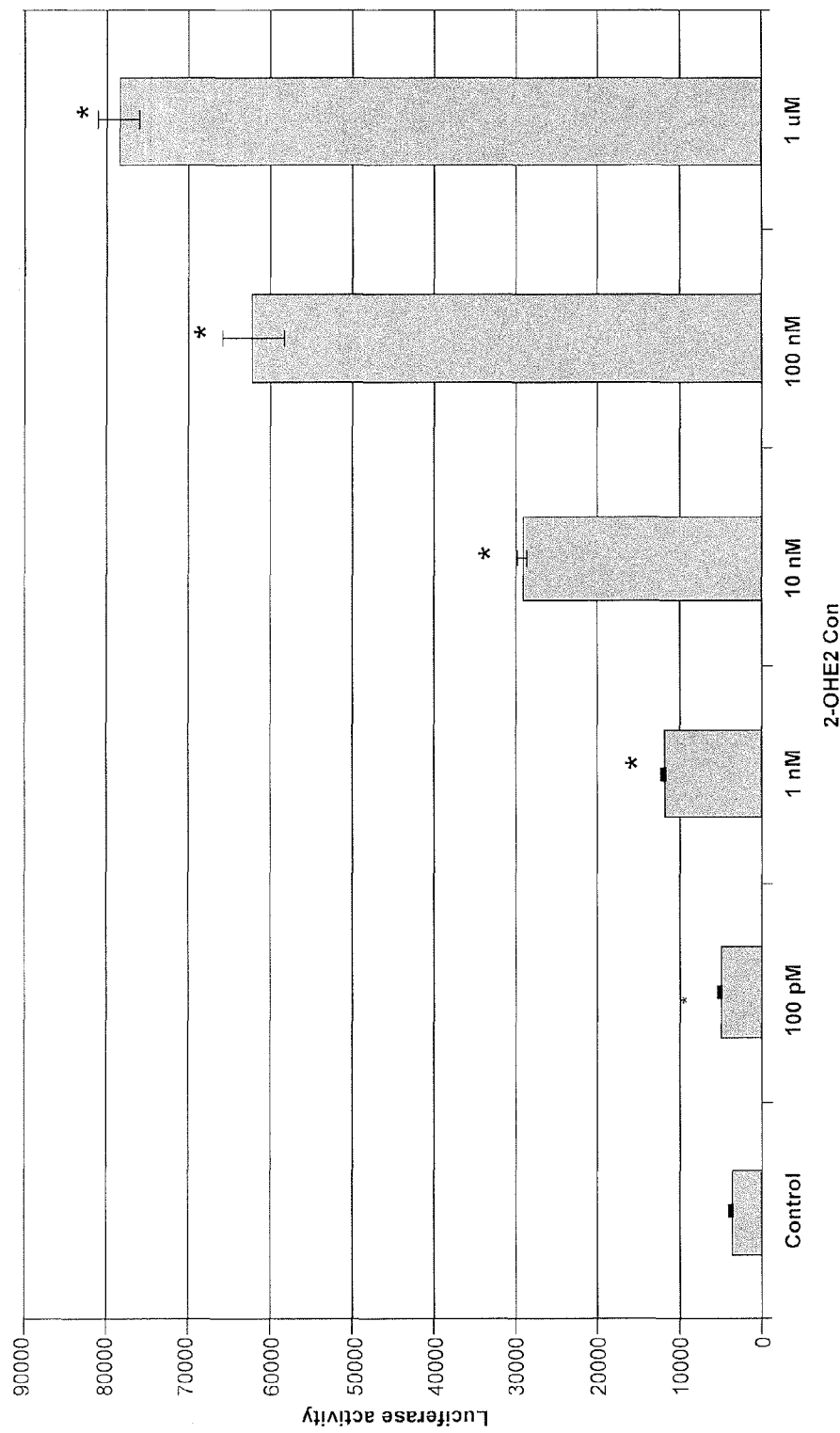
FIG. 9. Effect of 2-OHE2 alone (no E2) on Luciferase activity in ELT3 cells infected with AdERE-Luc. * indicates significantly higher levels of activity relative to the untreated control ($p<0.05$). "uM" means µM.
Figure 10:
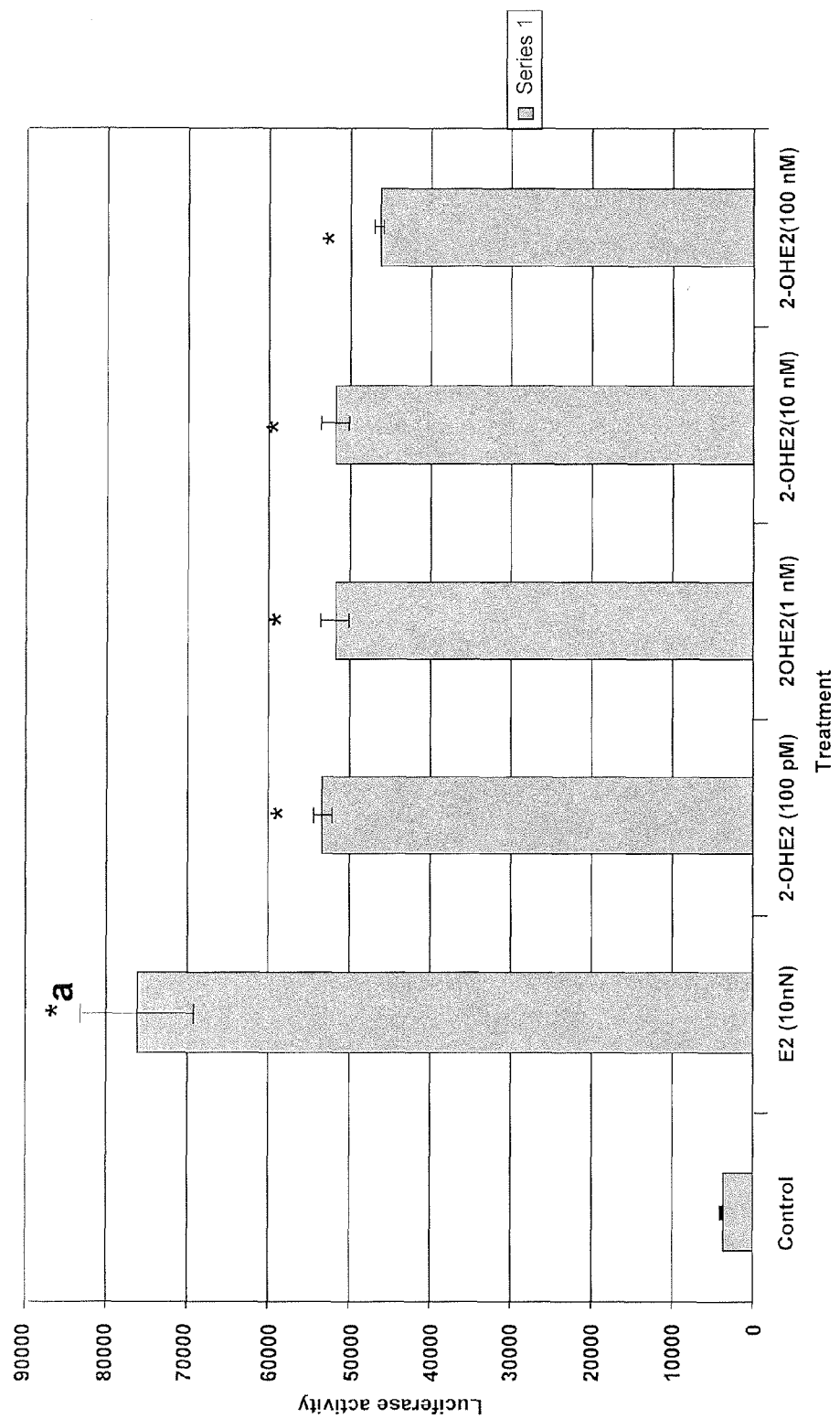
FIG. 10. Effect of 2-hydroxyestradiol on Luciferase activity in ELT3 cells transfected with AdERE-Luc reporter vector. *a indicates a level that is significantly different compared to the control and 2-OHE2-treated cells. * indicates a level significantly different from the control ($P<0.05$).

Previous studies reported that catechol estrogen 2-OHE2 binds to estrogen receptor and has weak estrogenic effect (Schutze et al., 1993). To test the whether 2-OHE2 can bind estrogen receptor and activated estrogen response elements in Leiomyomas cells, the effect of 2-OHE2 on AdERE-Luc reporter gene was investigated in ELT3 cells. As indicated in FIG. 9 in E2-free environment, 2-OHE2 up-regulated AdERE-Luc activity in a concentration dependent manner. In the presence of E2 ($10^{-8}$ M), treatment with 2-OHE2 resulted in down regulation of luciferase activity compared to treatment with E2 ($10^{-8}$ M) alone. The luciferase activity was reduced by 30%, 32%, 32%, and 39% at 2-OHE2 concentrations of $10^{-10}$ to $10^{-9}$, or $10^{-8}$, $10^{-7}$, and $10^{-6}$ M, respectively, compared to E2 ($10^{-8}$ M) treatment alone (FIG. 10). A similar inhibitory effect on AdERE-luc activity was observed when COMT inhibitor was used with 2-OHE2 and no E2 or with 2-OHE2 plus E2 (FIG. 11).

Concentration-Dependent Biphasic Effect of 2-MeOHE2 on the Proliferation of ELT3 Cells To evaluate the effects of estrogen metabolite 2-MeOHE2 on the proliferation of ELT3 cells, cells were treated with a wide concentration range ($10^{-10}$ to $10^{-5}$ M) of 2-MeOHE2. As indicated in FIG. 12, at a low concentration range of 2-MeOHE2, ($10^{-10}$, $10^{-9}$, $10^{-8}$ and $5\times10^{-8}$ M), the cell proliferation increased by 15%, 20%, 24% and 31%, respectively, from the untreated control. However, at higher concentrations ($10^{-7}$, $5\times10^{-7}$, $10^{-6}$, or $10^{-5}$ M) 2-MeOHE2 exerted a significant antiproliferative effect on ELT3 cells. At these high concentrations of 2-MeOHE2, the cell proliferations were reduced by 16%, 30%, 51%, and 65%, respectively, compared to the corresponding control. Furthermore, our data indicated that proliferative/antiproliferative effects of 2-OHE2 and 2-MeOHE2 were similar (FIG. 13)

Antiproliferative Effect of 2-MeOHE2 is Mediated via Estrogen-Regulated Genes

To investigate the possible mechanism of the effect of 2-MeOHE2 on ELT3 cells proliferation, its effect on the protein expression of several estrogen regulated genes, Bax and Bcl2, apoptosis-associated proteins, vascular endothelial growth factor (VEGF), and Cyclin D was investigated. Based on Western Blots, there was concentration-dependent inhibition of VEGF, cyclin D1, and Bcl2 protein expression in 2-MeOHE2-treated ELT3 leiomyoma cells with maximal inhibition achieved at 10 μM concentration. On the other hand, 2-MeOHE2 induced a gradient increase in Bax protein expression in a similar fashion.

All of the compositions and/or methods and/or apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,282,287
U.S. Pat. No. 4,542,102
U.S. Pat. No. 4,582,788
U.S. Pat. No. 4,656,127
U.S. Pat. No. 4,659,774
U.S. Pat. No. 4,682,195
U.S. Pat. No. 4,683,194
U.S. Pat. No. 4,683,195
U.S. Pat. No. 4,683,202
U.S. Pat. No. 4,800,159
U.S. Pat. No. 4,816,571
U.S. Pat. No. 4,879,236
U.S. Pat. No. 4,883,750
U.S. Pat. No. 4,946,773
U.S. Pat. No. 4,959,463
U.S. Pat. No. 5,141,813
U.S. Pat. No. 5,143,854
U.S. Pat. No. 5,202,231
U.S. Pat. No. 5,242,974
U.S. Pat. No. 5,252,743
U.S. Pat. No. 5,264,566
U.S. Pat. No. 5,279,721
U.S. Pat. No. 5,288,644
U.S. Pat. No. 5,324,633
U.S. Pat. No. 5,354,855
U.S. Pat. No. 5,384,261
U.S. Pat. No. 5,405,783
U.S. Pat. No. 5,412,087
U.S. Pat. No. 5,424,186
U.S. Pat. No. 5,428,148
U.S. Pat. No. 5,429,807
U.S. Pat. No. 5,432,049
U.S. Pat. No. 5,436,327
U.S. Pat. No. 5,445,934
U.S. Pat. No. 5,468,613
U.S. Pat. No. 5,470,710
U.S. Pat. No. 5,472,672
U.S. Pat. No. 5,492,806
U.S. Pat. No. 5,503,980
U.S. Pat. No. 5,510,270
U.S. Pat. No. 5,525,464
U.S. Pat. No. 5,527,681
U.S. Pat. No. 5,529,756
U.S. Pat. No. 5,532,128
U.S. Pat. No. 5,545,531
U.S. Pat. No. 5,547,839
U.S. Pat. No. 5,554,501
U.S. Pat. No. 5,554,744
U.S. Pat. No. 5,556,752
U.S. Pat. No. 5,561,071
U.S. Pat. No. 5,571,639
U.S. Pat. No. 5,574,146

U.S. Pat. No. 5,580,726
U.S. Pat. No. 5,580,732
U.S. Pat. No. 5,582,981
U.S. Pat. No. 5,593,839
U.S. Pat. No. 5,599,672
U.S. Pat. No. 5,599,695
U.S. Pat. No. 5,602,244
U.S. Pat. No. 5,610,287
U.S. Pat. No. 5,624,711
U.S. Pat. No. 5,631,134
U.S. Pat. No. 5,639,603
U.S. Pat. No. 5,645,897
U.S. Pat. No. 5,650,298
U.S. Pat. No. 5,654,413
U.S. Pat. No. 5,658,734
U.S. Pat. No. 5,661,028
U.S. Pat. No. 5,665,547
U.S. Pat. No. 5,667,972
U.S. Pat. No. 5,695,940
U.S. Pat. No. 5,700,637
U.S. Pat. No. 5,705,629
U.S. Pat. No. 5,744,305
U.S. Pat. No. 5,756,291
U.S. Pat. No. 5,780,610
U.S. Pat. No. 5,792,613
U.S. Pat. No. 5,800,992
U.S. Pat. No. 5,807,522
U.S. Pat. No. 5,830,645
U.S. Pat. No. 5,837,196
U.S. Pat. No. 5,840,867
U.S. Pat. No. 5,843,650
U.S. Pat. No. 5,846,709
U.S. Pat. No. 5,846,783
U.S. Pat. No. 5,847,219
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,871,928
U.S. Pat. No. 5,871,986
U.S. Pat. No. 5,876,932
U.S. Pat. No. 5,882,864
U.S. Pat. No. 5,912,148
U.S. Pat. No. 5,916,776
U.S. Pat. No. 5,916,779
U.S. Pat. No. 5,919,626
U.S. Pat. No. 5,922,574
U.S. Pat. No. 5,928,905
U.S. Pat. No. 5,928,906
U.S. Pat. No. 5,932,451
U.S. Pat. No. 5,935,825
U.S. Pat. No. 5,939,291
U.S. Pat. No. 5,942,391
U.S. Pat. No. 6,004,755
U.S. Pat. No. 6,087,102
U.S. Pat. No. 6,368,799
U.S. Pat. No. 6,383,749
U.S. Pat. No. 6,617,112
U.S. Pat. No. 6,638,717
U.S. Pat. No. 6,720,138
Abdel-Rahman et al., *J. Biochem. Toxicol.*, 9:191-198, 1994.
Al-Hendy and Luxon, *J. Soc. Gynecol. Investig.*, 9(1):744, 2002.
Al-Hendy et al., *J. Soc. Gynecol. Investig.*, 9(1):794, 2002.
Andersen et al., *J. Soc. Gynecol. Investig.*, 2:542-551, 1995.
Axelrod and Tomchick, *J. Biol. Chem.*, 233:702-705, 1958.
Baichwal and Sugden, In: *Gene Transfer*, Kucherlapati (Ed.), NY, Plenum Press, 117-148, 1986.
Ball and Knuppen, *Acta Endocrinol. Suppl. (Copenh)*, 232:1-127, 1980.
Balloch, In: *The relative frequency of fibroid processes in the dark-skinned races*, Medical News, 29-35, 1984.
Banerjee et al., *Neoplasia*, 5(5):417-426, 2003.
Banerjeei et al., *Anticancer Res.*, 20(4):2641-2645, 2000.
Barany and Merrifield, In: *The Peptides*, Gross and Meienhofer (Eds.), Academic Press, NY, 1-284, 1979.
Barchiesi et al., *Hypertension.*, 42:420, 2003.
Bellus, *J. Macromol. Sci. Pure Appl. Chem.*, A31(1): 1355-1376, 1994.
Berzal-Herranz et al., *Genes Dev*, 6(1):129-134, 1992.
Brandon et al., *J. Clin. Endocrinol. Metab.*, 80:1876-1881, 1995.
Brummelkamp et al., *Science*, 296(5567):550-553, 2002.
Bruno et al., *Lancet. Oncol.*, 5(7):430-442, 2004.
Burgstaller et al., *Curr. Opin. Drug Discov. Devel.*, 5(5):690-700, 2002.
Buttram and Reiter, *Fertil. Steril.*, 36:433-445, 1981.
Carlson et al., *Obstet. Gynecol.*, 83:556-565, 1994.
Carlson et al., *Obstet. Gynecol.*, 83:566-572, 1994.
Cech et al., *Cell*, 27(3 Pt 2):487-496, 1981.
Chegini et al., *J. Soc. Gynecol. Investig.*, 10:161-171, 2003.
Chiaffarino et al., *Br. J. Obstet. Gynaecol.*, 106:857-860, 1999.
Chiaffarino et al., *Obstet. Gynecol.*, 94:395-398, 1999.
Chowrira et al., *J. Biol. Chem.*, 268:19458-62, 1993.
Chowrira et al., *J. Biol. Chem.*, 269(41):25856-25864, 1994.
Coligan et al., *Current Protocols in Immunology*, 1(2): Chapter 5, 1991.
Cook and Walker, *Semin. Reprod. Med.*, 22(2):105-111, 2004.
Coronado et al., *Obstet. Gynecol.*, 95:764-769, 2000.
Coupar et al., *Gene*, 68:1-10, 1988.
Cramer and Patel, *Am. J. Clin. Pathol.*, 94:435-438, 1990.
Culver et al., *Science*, 256(5063):1550-1552, 1992.
Dawood et al., *Fertil. Steril.*, 52:21-26, 1989.
Deligdish and Loewenthal, *J. Clin. Pathol.*, 23:676-680, 1970.
Dubey et al., *Arterioscler. Thromb. Vasc. Biol.*, 20:964-972, 2000.
Dunlap, In: *Immobilized Biochemicals and Affinity Chromatography*, Adv. Exp. Med. Biol. 42, Plenum Press, N.F. 1974
Elbashir et al., *Genes Dev.*, 5(2):188-200, 2001.
European Appln. 201,184
European Appln. 237,362
European Appln. 258,017
European Appln. 266,032
European Appln. 320 308
European Appln. 329 822
European Appln. 373 203
European Appln. 50,424
European Appln. 785 280
European Appln. 799 897
European Appln. 84,796
Feigelson and Henderson, *Carcinogenesis*, 17(11):2279-2284, 1996.
Figg et al., *Invest. New Drugs*, 20(2):183-194, 2002.
Flake et al., *Environ. Health Perspect.*, 111(8):1037-1054, 2003.
Forster and Symons, *Cell*, 49(2):211-220, 1987.
French Appln. 2,650,840
Friedmann, *Science*, 244:1275-1281, 1989.
Frisch et al., *Mol. Psychiatry*, 6:243-245, 2001.

Froehler et al., *Nucleic Acids Res.*, 14(13):5399-5407, 1986.
Frohman, In: *PCR Protocols: A Guide To Methods And Applications*, Academic Press, N.Y., 1994.
Fuchs-Young et al., *Mol. Carcinog.*, 17:151-159, 1996.
GB Appln. 2 202 328
GB Appln. 8 803 000
Gerlach et al., *Nature (London)*, 328:802-805, 1987.
Ghosh et al., *Melanoma Res.*, 13(2): 119-127, 2003.
Goodman et al., *Carcinogenesis*, 22:1661-1665, 2001.
Gordon et al., *Curr. Opin. Obstet. Gynecol.*, 15(5):377-384., 2003.
Gossen and Bujard, *Proc. Natl. Acad. Sci. USA*, 89:5547-5551, 1992.
Gossen et al., *Science*, 268(5218):1766-1769, 1995.
Gupta et al., *J. Steroid Biochem. Mol. Biol.*, 67(5-6):413-419, 1998.
Harlow and Lane, In: *Antibodies: A Laboratory Manual*, Cold Spring Harbor Laboratory, Cold Spring Harbor, N.Y., 346-348, 1988.
Haseloff and Gerlach, *Nature*, 334:585-591, 1988.
Hidalgo et al., *Adv. Intern Med.*, 47:159-190, 2001.
Horwich et al. *J. Virol.*, 64:642-650, 1990.
Houghten et al., *Infect. Immun.*, 48(3):735-740., 1985.
Howe et al., *Am. J. Pathol.*, 146:1568-1579, 1995.
Howe et al., *Endocrinology*, 136:4996-5003, 1995.
Hsieh et al., *Fertil. Steril.*, 79:96-99, 2003.
Huang et al., *Cancer Res.*, 59:4870-4875, 1999.
Hunter et al., *Environ. Health Perspect.*, 108(5):829-834, 2000.
Jakoby and Wilchek, *Methods Enzymol.*, 34:3-10, 1974.
Joyce, *Nature*, 338:217-244, 1989.
Kim and Cech, *Proc. Natl. Acad. Sci. USA*, 84(24):8788-92, 1987.
Kitawaki et al., *Hum. Reprod.*, 16:51-55, 2001.
Kjerulff et al., *J. Reprod. Med.*, 41:483-490, 1996.
Kjerulff et al., *Obstet. Gynecol.*, 82:757-764, 1993.
Kjerulff et al., *Obstet. Gynecol.*, 95:319-326, 2000.
Komher, et al., *Nucl. Acids. Res.* 17:7779-7784, 1989.
Kuppuswamy, et al., *Proc. Natl. Acad. Sci. USA*, 88:1143-1147, 1991.
Lachman et al., *Pharmacogenetics*, 6:243-250, 1996.
Landegren, et al., *Science* 241:1077-1080, 1988.
Lavigne et al., *Cancer Res.*, 57:5493-5497, 1997.
Lethaby et al., *Update Software Ltd.*, The Cochrane Library, 2001.
Lieber and Strauss, *Mol. Cell. Biol.*, 15(1):540-551, 1995.
Linde, In: *Operative Gynecology*, Rock and Thompson (Eds.), Philadelphia: Lippincott-Raven; 732, 1997.
Mabjeesh et al., *Cancer Cell*, 3(4):363-375, 2003.
Marshall et al., *Epidemiology*, 9:511-517, 1998.
Marshall et al., *Fertil. Steril.*, 70:432-439, 1998.
Marshall et al., *Obstet. Gynecol.*, 90:967-973, 1997.
Martel et al., *Semin. Reprod. Med.*, 22(2):91-103, 2004.
Massart et al., *Fertil Steril.*, 75:567-570, 2001.
Matsuo et al., *J. Clin Endocrinol Metab.* 82:293-299, 1997.
Maxam, et al., *Proc. Natl. Acad. Sci. USA*, 74:560, 1977.
McLachlan et al., *Br. J. Obstet. Gynecol.*, 93:431-454, 1986.
McLeod et al., *J. Pharmacol. Exp. Ther.*, 270:26-29, 1994.
Merrifield, *Science*, 232(4748):341-347, 1986.
Michel and Westhof, *J. Mol. Biol.*, 216:585-610, 1990.
Mitrunen et al., *Cancer Epidemiol. Biomarkers Prev.*, 10:635-640, 2001.
Mooberry, *Curr. Opin. Oncol.*, 15(6):425-430, 2003.
Mooberry, *Drug Resist Updat.*, 6(6):355-361, 2003.
Mullis et al., *Cold Spring Harbor Symp. Quant. Biol.* 51:263-273, 1986.
Nickerson et al., *Proc. Natl. Acad. Sci. USA*, 87:8923-8927, 1990.
Nicolas and Rubenstein, In: *Vectors: A survey of molecular cloning vectors and their uses*, Rodriguez and Denhardt (Eds.), Stoneham: Butterworth, 494-513, 1988.
Nowak, *Clin. Obstet. Gynecol.*, 44(2):327-334, 2001.
Nowak, *Environ. Health Perspect.*, 108(5):849-853, 2000.
Nyren et al., *Anal. Biochem.* 208:171-175, 1993.
Ohara et al., *Proc. Natl. Acad. Sci. USA*, 86:5673-5677, 1989.
Palukaitis et al., *Virology*, 99:145-151, 1979.
Parazzini et al., *Epidemiology*, 7:440-442, 1996.
Parazzini et al., *J. Reprod. Med.*, 41:316-320, 1996.
Patrikis et al., *Mol. Carcinog.*, 37:61-64, 2003.
PCT Appln. PCT/US87/00880
PCT Appln. PCT/US89/01025
PCT Appln. WO 0138580
PCT Appln. WO 0168255
PCT Appln. WO 03/012052
PCT Appln. WO 03020898
PCT Appln. WO 03022421
PCT Appln. WO 03023058
PCT Appln. WO 03029485
PCT Appln. WO 03040410
PCT Appln. WO 03053586
PCT Appln. WO 03066906
PCT Appln. WO 03067217
PCT Appln. WO 03076928
PCT Appln. WO 03087297
PCT Appln. WO 03091426
PCT Appln. WO 03093810
PCT Appln. WO 03100012
PCT Appln. WO 03100448A1
PCT Appln. WO 04020085
PCT Appln. WO 04027093
PCT Appln. WO 84/03564
PCT Appln. WO 88/10315
PCT Appln. WO 89/06700
PCT Appln. WO 90/07641
PCT Appln. WO 93/17126
PCT Appln. WO 95/11995
PCT Appln. WO 95/21265
PCT Appln. WO 95/21944
PCT Appln. WO 95/35505
PCT Appln. WO 96/31622
PCT Appln. WO 97/10365
PCT Appln. WO 97/27317
PCT Appln. WO 97/43450
PCT Appln. WO 99/23256
PCT Appln. WO 99/35505
PCT Appln. WO 99/36760
PCT Appln. WO91/02087
PCT Appln. WO92/15712
PCT Pubn. 90/07582
PCT Pubn. 91/00868
PCT Pubn. 91/07087
Perriman et al., *Gene*, 113:157-163, 1992.
Perrotta and Been, *Biochemistry*, 31(1): 16-21, 1992.
Pollow et al., *J. Clin. Chem. Clin. Biochem.*, 16:493-502, 1978.
Prezant et al., *Hum. Mutat.*, 1: 159-164, 1992.
Prody et al., *Science*, 231:1577-1580, 1986.
Reddy et al., *Steroids*, 37:195-203, 1981.
Reenila, In: *Catechol-O-Methyltransferase Activity: Assay, Distribution and Pharmacological Modification*, Helsinki, 1999.

Reinhold-Hurek and Shub, *Nature*, 357:173-176, 1992. Remington's Pharmaceutical Sciences, 18th Ed. Mack Printing Company, pp. 1289-1329, 1990.
Rice et al., *Am. J. Obstet. Gynecol.*, 160:1212-1216, 1989.
Ridgeway, In: *Vectors: A survey of molecular cloning vectors and their uses*, Rodriguez and Denhardt (Eds.), Stoneham: Butterworth, 467-492, 1988.
Ross et al., *BMJ*, 293:359-362, 1986.
Rowe et al., *Obstet. Gynecol.*, 93:915-921, 1999.
Sambrook et al., In: *Molecular cloning*, Cold Spring Harbor Laboratory Press, Cold Spring Harbor, N.Y., 2001.
Sanger, et al., *J. Molec. Biol.*, 94:441, 1975.
Sarver et al., *Science*, 247:1222-1225, 1990.
Scanlon et al., *Proc. Natl. Acad. Sci. USA*, 88:10591-10595, 1991.
Schneider et al., *J. Biol. Chem.*, 259(8):4840-4845, 1984.
Schutze et al., *J. Steroid Biochem. Mol. Biol.*, 46(6):781-789, 1993.
Schwartz et al., *Environ. Health Perspect.*, 108(5):821-827, 2000.
Sioud et al., *J. Mol. Biol.*, 223:831-835, 1992.
Sokolov, *Nucl. Acids Res.* 18:3671, 1990.
Stewart and Young, In: *Solid Phase Peptide Synthesis*, 2d. ed., Pierce Chemical Co., 1984.
Stewart et al., *J. Clin. Endocrinol. Metab.*, 79:900-906, 1994.
Sui et al., *Proc. Natl. Acad. Sci. USA*, 99(8):5515-5520, 2002.
Swaneck et al., *Proc. Natl. Acad. Sci. USA*, 85(21):7831-7835, 1988.
Symons, *Annu. Rev. Biochem.*, 61:641-671, 1992.
Symons, *Nucl. Acids Res.*, 9(23):6527-6537, 1981.
Syvanen et al., *Am. J. Hum. Genet.*, 52(1):46-59, 1993.
Syvanen et al., *Genomics*, 8:684-692, 1990.
Tam et al., *J. Am. Chem. Soc.*, 105:6442, 1983.
Temin, In: *Gene Transfer*, Kucherlapati (Ed.), NY, Plenum Press, 149-188, 1986.
Thompson et al., *Cancer Res.*, 58, 2107-2110, 1998.
Thompson et al., *Nature Genet.*, 9:444-450, 1995.
Torpin et al., *Am. J. Obstet. Gynecol.*, 44:569-574, 1942.
Tsibris et al., *Fertil. Steril.*, 78:114-121, 2002.
Ugozzoll et al., *GATA* 9:107-112, 1992.
Van Aswegen et al., *J. Steroid Biochem.*, 32(4):485-492, 1989.
Vandewalle et al., *Mol. Cell. Endocrinol.*, 61(2):239-246, 1989.
Walker et al., *Genes Chromosomes Cancer*, 38(4):349-356, 2003.
Walker et al., *Genes Chromosomes Cancer*, 38(4):349-356, 2003.
Walker et al., *Proc. Natl. Acad. Sci. USA*, 89:392-396 1992.
Walker, *Recent Prog. Horm. Res.*, 57:277-294, 2002.
Weismiller, *Am. Fam. Physician*, 59(3):593-602, 1999.
Wilcox et al., *Obstet. Gynecol.*, 83:549-555, 1990.
Wilson, In: *Polycystic Kidney Disease*, Watson and Torres (Eds.), Oxford Medical Publications; 125-163, 1996.
Witherspoon and Butler, *Surg. Gynecol. Obstet.*, 58:57-61, 1934.
Xie et al., *Proc. Am. Assoc. Cancer Res.*, 40:3744, 1999.
Yim et al., *Pharmacogenetics*, 11:279-286, 2001.
Yuan and Altman, *Science*, 263:1269-1273, 1994.
Yuan et al., *Proc. Natl. Acad. Sci. USA*, 89:8006-8010, 1992.
Zacharia et al, *Circulation*, 108(24):2974-2978, 2003.
Zacharia et al., *J. Pharmacol. Exp. Ther.*, 309(3):1093-1097, 2004.
Zaloudek and Hendrickson In: *Blaustein's Pathology of the Female Fenital Tract*, Springer-Verlag (Ed.), 5th Ed., NY, 561-615, 2002.
Zhu and Connery, *Cancer Res.*, 58:2269-2277, 1998.
Zhu and Conney, *Carcinogenesis*, 19:1-27, 1998.
Zhu and Conney, *Carcinogenesis*, 19:1-27, 1998.
Zhu, *Curr Drug Metab.*, 3(3):321-349, 2002.

The invention claimed is:

1. A method of diagnosing a subject as at risk for developing or as having a leiomyoma comprising measuring in a sample from the subject catechol-O-methyltranferase (COMT) levels, and/or COMT activity, wherein an increase in COMT levels and/or COMT activity, as compared to a normal reference, indicates that the subject is at risk for developing or has a leiomyoma.

2. The method of claim 1, wherein measuring COMT activity is by measurement of COMT substrate and/or COMT product in a sample.

3. The method of claim 2, wherein the COMT substrate is a hydroxyestrogen.

4. The method of claim 3, wherein the COMT substrate is 2-hydroxyestradiol or 4-hydroxyestradiol.

5. The method of claim 2, wherein the COMT product is a methylated hydroxyestrogen.

6. The method of claim 5, wherein the COMT product is 2-methoxyestradiol or 4-methoxyestradiol.

7. The method of claim 6, wherein the COMT product is 2-methoxyestradiol.

8. The method of claim 1, further comprising comparing COMT levels in the subject with COMT levels in a second subject with no indications of a leiomyoma, wherein an increase in COMT activity, elevated COMT product levels, and/or decreased COMT substrate levels indicate that the subject is at risk for developing a leiomyoma.

9. The method of claim 1, further comprising determining methylated catechol estrogen level in the sample, wherein an increase in the level indicates a risk of a leiomyoma.

10. The method of claim 1, further comprising taking a family history or a patient history.

11. The method of claim 1, wherein the COMT level is the level of COMT protein.

12. The method of claim 11, wherein measuring the amount of COMT comprising antibody recognition of a COMT polypeptide.

13. The method of claim 12, wherein the antibody is selected from the group consisting of a polyclonal antibody, monoclonal antibody, humanized antibody, single chain antibody, Fab fragment and bispecific antibody.

14. The method of claim 11, wherein measuring COMT levels or COMT activity comprises using an array or biochip.

15. The method of claim 1, wherein the COMT level is the level of COMT nucleic acids.

16. The method of claim 1, wherein measuring COMT levels or COMT activity comprises a binding assay selected from a gel electrophoresis, a gel filtration chromatography, a fluorescence quenching, a flow cytometry, an ELISA, a solid phase immunoassay, or a confocal microscopy assay.

17. The method of claim 1, wherein the sample comprises blood, urine, serum, pap smear, a genitourinary tract tissue, or a endometrial tissue.

18. The method of claim 1, further comprising obtaining a sample from the patient.

* * * * *